United States Patent
Gianneschi et al.

(10) Patent No.: US 11,530,240 B2
(45) Date of Patent: Dec. 20, 2022

(54) CATHETER INJECTABLE CYCLIC PEPTIDE PRO-GELATORS FOR MYOCARDIAL TISSUE ENGINEERING

(71) Applicant: The Regents of the University of California, Oakland, CA (US)

(72) Inventors: Nathan C. Gianneschi, Evanston, IL (US); Karen L. Christman, La Jolla, CA (US); Andrea S. Carlini, Evanston, IL (US)

(73) Assignee: The Regents of the University of California, Oakland, CA (US)

( * ) Notice: Subject to any disclaimer, the term of this patent is extended or adjusted under 35 U.S.C. 154(b) by 308 days.

(21) Appl. No.: 16/620,025

(22) PCT Filed: Jun. 11, 2018

(86) PCT No.: PCT/US2018/036901
§ 371 (c)(1),
(2) Date: Dec. 6, 2019

(87) PCT Pub. No.: WO2018/227187
PCT Pub. Date: Dec. 13, 2018

(65) Prior Publication Data
US 2021/0054027 A1    Feb. 25, 2021

Related U.S. Application Data

(60) Provisional application No. 62/517,213, filed on Jun. 9, 2017.

(51) Int. Cl.
| | |
|---|---|
| C07K 7/08 | (2006.01) |
| A61P 9/10 | (2006.01) |
| A61K 9/00 | (2006.01) |
| A61K 38/10 | (2006.01) |
| A61K 45/06 | (2006.01) |
| A61L 27/52 | (2006.01) |
| A61L 27/54 | (2006.01) |
| A61M 25/00 | (2006.01) |

(52) U.S. Cl.
CPC .............. *C07K 7/08* (2013.01); *A61K 9/0019* (2013.01); *A61K 9/0029* (2013.01); *A61K 38/10* (2013.01); *A61K 45/06* (2013.01); *A61L 27/52* (2013.01); *A61L 27/54* (2013.01); *A61P 9/10* (2018.01); *A61L 2300/412* (2013.01); *A61L 2300/414* (2013.01); *A61L 2400/06* (2013.01); *A61L 2430/20* (2013.01); *A61M 25/00* (2013.01); *A61M 2210/125* (2013.01)

(58) Field of Classification Search
CPC ........ A61K 38/00; A61K 38/10; A61K 45/06; A61K 9/0019; A61K 9/0029; A61L 2300/412; A61L 2300/414; A61L 2400/06; A61L 2430/20; A61L 27/227; A61L 27/52; A61L 27/54; A61M 25/00; A61M 2210/125; A61P 9/10; C07K 2319/50; C07K 2319/70; C07K 7/08
See application file for complete search history.

(56) References Cited

U.S. PATENT DOCUMENTS

| | | |
|---|---|---|
| 2003/0166138 A1* | 9/2003 | Kinsella ................ C07K 5/126 435/325 |
| 2009/0060924 A1 | 3/2009 | Korytko et al. |
| 2010/0016548 A1 | 1/2010 | Yokoi et al. |
| 2011/0165242 A1 | 7/2011 | Su et al. |
| 2013/0338633 A1 | 12/2013 | Basu et al. |
| 2015/0197359 A1 | 7/2015 | Nohara et al. |
| 2015/0274789 A1 | 10/2015 | Guerette et al. |
| 2016/0220687 A1 | 8/2016 | Alhamdan |
| 2019/0375796 A1* | 12/2019 | Touti ................ G01N 33/54393 |
| 2021/0002306 A1* | 1/2021 | Foley ..................... A61K 45/06 |

FOREIGN PATENT DOCUMENTS

WO    2016/159886 A1    10/2016

OTHER PUBLICATIONS

PCT International Search Report and Written Opinion for PCT Application No. PCT/US2018/036901 dated Sep. 10, 2018 (11 pages).

\* cited by examiner

*Primary Examiner* — Marcela M Cordero Garcia
(74) *Attorney, Agent, or Firm* — Eversheds Sutherland (US) LLP

(57) ABSTRACT

Cyclic peptide pro-gelator compositions, and methods of therapeutic use, which assemble into macromolecular hydrogel when administered through cleavage by endogenous enzymes upregulated at a site of tissue injury, such as a myocardial infarction.

18 Claims, 19 Drawing Sheets
Specification includes a Sequence Listing.

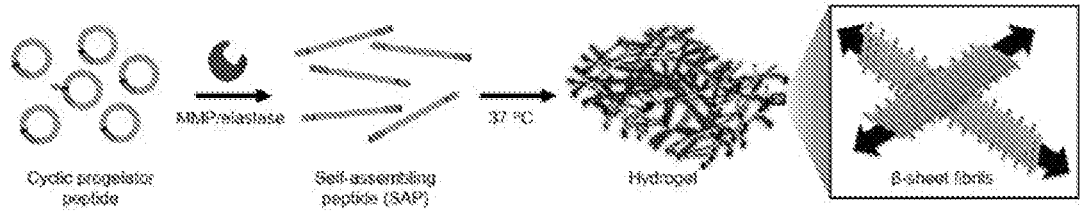
FIG. 1a  FIG. 1b  FIG. 1c
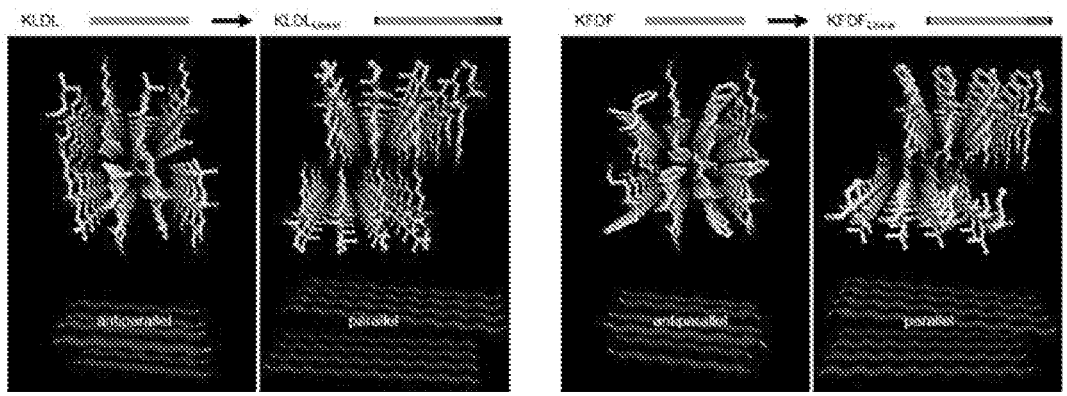
Fig. 2a
Fig. 2b  Fig. 2c

CATHETER INJECTABLE CYCLIC PEPTIDE PRO-GELATORS FOR MYOCARDIAL TISSUE ENGINEERING

CROSS REFERENCE TO RELATED APPLICATION

This application claims the priority benefit of PCT/US2018/036901 filed on Jun. 11, 2018 which claims the priority benefit to U.S. Provisional Patent Application No. 62/517,213, filed Jun. 9, 2017, the entire contents of which are incorporated by reference.

STATEMENT OF GOVERNMENT INTEREST

This invention was made with government support under Grant No. 5R01HL117326 awarded by National Institutes of Health (NIH) and Grant No. DGE-1144086 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Jun. 11, 2018, is named 24978-0403_SL.txt and is 25,497 bytes in size.

BACKGROUND OF THE INVENTION

Myocardial infarction (MI) accounts for 46% of all deaths attributed to cardiovascular disease.[1] Within the first few days post-MI, an inflammatory response causes cardiomyocyte death and degradation of the native extracellular matrix (ECM) by secreted matrix metalloproteinases (MMPs).[2] This in turn can lead to aneurysmal thinning and negative left ventricular (LV) remodeling within days to weeks. Left untreated, heart failure results as one of the leading causes of death in the western world.

Injectable hydrogel-based scaffolds have gained attention as a therapeutic approach to prevent negative LV remodeling by utilizing materials to stimulate cardiac repair. Materials for this purpose have included myocardial ECM,[3] alginate,[4] and hyaluronic acid hydrogels,[5] or employing biomaterials as therapeutic delivery scaffolds such as naturally derived polymeric hydrogels (e.g. collagen,[6] fibrin,[7] heparin,[8] and gelating), synthetic polymeric hydrogels (e.g. PNIPAAm,[10] ureido-pyrimidinone-modified PEG,[11] and chitosan[12]) and microparticles (e.g. PLGA[13] and dextran[14]). Despite many successful preclinical studies, wide spread translation and initiation of clinical trials has been slow, with current studies limited to a myocardial ECM hydrogel (clinicaltrials.gov identifier NCT02305602) and alginate (NCT01226563 and NCT01311791). One reason for this lack of translation is that the majority of these hydrogels are not candidates for minimally invasive catheter delivery because of excess material viscosity, their quick gelling nature that can lead to catheter clogging, and concerns regarding hemocompatibility since materials can leak into the blood stream upon injection into a beating heart.[15-17]

One versatile class of materials that has been successfully tested in several preclinical MI models using surgical epicardial injections is self-assembling peptides (SAPs).[18-21] SAP hydrogels are attractive as they: (1) resemble native ECM, (2) require no additive reagents to induce gelation, (3) are biodegradable, (4) are biocompatible, (5) have pore sizes (~5-200 nm) conducive to promote endothelial cell adhesion and capillary formation, (6) allow rapid cellular migration because of their flexibility, (7) are rehealable, (8) do not suffer from batch-to-batch chemical variability, and (9) are amenable to sequence modification.[22,23] However, SAPs have not been demonstrated as being amenable to cardiac injection catheter delivery. Other researchers have considered efforts with enzyme-responsive peptides[24-26] and a study by Nilsson and coworkers utilizing reductively triggered cyclic peptides as progelators[27] but the art has not provided cyclic, enzyme triggered, responsive peptide platform that enables minimally invasive delivery of self assembling peptides to the heart. It was previously demonstrated that peptide-polymer based nanoparticles can aggregate into macromolecular scaffolds in diseased tissue through the action of endogenously expressed inflammatory-related enzymes, matrix metalloproteinases (MMPs), providing a viable method for targeted accumulation,[28] prolonged tissue retention,[29] and therapeutic delivery.[30] However, these materials employed a non-biodegradable functionalized polynorbornene backbone and did not possess viscoelastic properties.

SUMMARY OF THE INVENTION

The invention provides a tissue scaffolding composition and method of use for treating tissues in need thereof, e.g., myocardial infarctions, comprising in various embodiments a cyclic peptide. In embodiments, the peptide comprises a substrate recognition sequence that when enzymatically cleaved linearizes and self assembles into a hydrogel. In embodiments, the peptide has at least one, preferably three or more, repeating amino acid sequence KFDF (SEQ ID NO:1) or KLDL (SEQ ID NO:5) or other known SAP gelling sequences. In embodiments, the peptide is made cyclic by containing covalent disulfide bonds on cysteine residues or other functional moieties. In embodiments, the substrate recognition sequence is specific for inflammatory-related enzymes, matrix metalloproteinases (MMP)-2/9 and/or elastase. In embodiments, the substrate recognition sequence comprises a MMP-2/9 cleavable amino acid sequence PLGLAG (SEQ ID NO:2). In embodiments, the peptide is labeled for detection or other functional moieties. In alternative embodiments, the composition further comprises a therapeutic agent, a chemotactic agent, an antibiotic, and/or a growth factor.

The invention provides a method of creating a scaffold for tissue repair in a patient in need thereof comprising administering to the patient a tissue scaffolding composition as described. In embodiments, the scaffold is used for example in negative left ventricular remodeling post-myocardial infarction. In embodiments, the administration is via a catheter, parenteral injection, or implantation.

In certain embodiments, the present invention provides compositions and methods comprising injecting or implanting in a subject in need an effective amount of the tissue scaffolding composition. The composition can further comprise cells, drugs, proteins, or polysaccharides. The composition can be delivered as a liquid, and can transition to a gel form after delivery and in situ enzymatic cleavage. In some instances, the composition is coated on a device such as an implant.

In some instances, the composition is configured to be delivered to a tissue through a catheter. In some instances, said composition is suitable for direct implantation into a patient.

In some instances the composition comprises cells, proteins, or therapeutic agents. In some instances, the composition further comprises non-naturally occurring factors that recruit cells into the composition, encourage growth or prevent infection. In some instances, the composition further comprises a therapeutic agent, and as such is configured as a drug delivery vehicle.

Enzyme-induced peptide assembly provides a sensitive method for minimally invasive delivery of scaffolding materials to the site of acute MI. Geling peptides bearing a substrate recognition sequence for the inflammatory-related enzymes, matrix metalloproteinase (MMP)-2/9 and elastase, were cyclized via disulfide bonds to create a water-soluble pro-gelator. When enzymatically cleaved, sterically constrained cyclic peptides linearize and self-assemble via beta-sheets into hydrogels, as shown by TEM, rheometry, and circular dichroism spectroscopy. Furthermore, incorporation of functional ligands and enzyme-responsive amino acids does not disrupt hydrogel assembly. Concentrated peptide solutions in saline were shown to be readily injectable via catheter delivery, representing the first example of a peptide-based gelator for delivery to the MI. Finally, enzyme activation of these materials results in hydrogels that exhibit repeated and rapid healing following excess shear strain. The invention provides compositions and methods for therapeutic hydrogel delivery to acute MI.

BRIEF DESCRIPTION OF THE DRAWINGS

FIGS. 1a-1c. Design of cyclic, enzyme-responsive progelator peptides for activatable gelation. FIG. 1a, cyclic progelator peptides, containing gelling sequence (green greyscales), MMP/elastase enzyme-cleavage recognition sequence (red greyscales), and disulfide bridge (black) resist assembly due to conformational constraint. Rhodamine labeled (pink ellipse greyscales) SAPs were employed for in vivo studies as a 5 mol % additive to provide a means for imaging the hydrogels in ex vivo microscopy analyses. FIG. 1b, Enzymatic cleavage results in linearization into SAPs. FIG. 1c, SAPs assemble into viscoelastic hydrogels composed of β-sheets fibrils.

FIGS. 2a-2c. Sequences and design of SAPs and cyclic, enzyme-responsive progelators. FIG. 2a, Table of SAPs and progelators based on the (KLDL)$_3$ (SEQ ID NO:3) and (KFDF)$_3$ (SEQ ID NO:4) amino acid gelling sequence with corresponding diagrammatical representations. Sequences are shown for the base, unmodified SAPs (KLDL (SEQ ID NO:5) and KFDF (SEQ ID NO:1)) and modified SAPs (KLDL (SEQ ID NO:5)$_{Linear}$ and KFDF (SEQ ID NO:1)$_{Linear}$) primed for cyclization but lacking fluorescent labels, together with the corresponding cyclized versions (progelators, KLDL (SEQ ID NO:5)$_{Cyclic}$ and KFDF (SEQ ID NO:1)$_{Cyclic}$). Peptide sequences CKLDLKLDLKLD-LPLGLAGC (SEQ ID NO:6) and CKFDFKFDFKFDFPLGLAGC ((SEQ ID NO:7) are compared. In addition, rhodamine labeled modified SAPs (Rho-KLDL (SEQ ID NO:5)$_{Linear}$ and Rho-KFDF (SEQ ID NO:1)$_{Linear}$) are shown, together with their corresponding labeled cyclized progelators (Rho-KLDL (SEQ ID NO:5)$_{Cyclic}$ and Rho-KFDF (SEQ ID NO:1)$_{Cyclic}$). "acm" denotes the acetamidomethyl protecting group on Cysteine residues. "Rho" designates the 5(6)-carboxytetramethyl rhodamine label. FIGS. 2b-2c, Modeling predicts β-sheet re-orientation, rather than self-assembly disruption, following significant SAP functionalization. FIG. 2b, Predicted structures and ribbon diagrams (bottom) of KLDL (SEQ ID NO:5) and KLDL (SEQ ID NO:5)$_{Linear}$ SAPs from FibPredictor simulations revealing antiparallel and parallel β-sheet orientations, respectively. FIG. 2c, Predicted structures and ribbon diagrams (bottom) of KFDF (SEQ ID NO:1) and KFDF (SEQ ID NO:1)$_{Linear}$ SAPs from FibPredictor simulations revealing antiparallel and parallel-sheet orientations, respectively (see Tables 1-2).

FIG. 3a, Experimental circular dichroism (CD) spectra of KLDL (SEQ ID NO:5) and KLDL (SEQ ID NO:5)$_{Linear}$ SAPs, with labeled minimum at 215 nm (n→π*). FIG. 3a discloses SEQ ID NO:7 as "C(KFDF)$_3$PLGLAGC". FIG. 3b, Experimental circular dichroism (CD) spectra of KFDF (SEQ ID NO:1) and KFDF (SEQ ID NO:1)$_{Linear}$ SAPs, with labeled minima at 215 nm (n→π*) and 203 nm (π→π*). FIG. 3c, Theoretical CD spectra of KLDL (SEQ ID NO:5) and KLDL (SEQ ID NO:5)$_{Linear}$ SAPs from DichroCalc simulations using FibPredictor models. FIG. 3d, Theoretical CD spectra of KFDF (SEQ ID NO:1) and KFDF (SEQ ID NO:1)$_{Linear}$ SAPs from DichroCalc simulations using FibPredictor models. CD spectra minima denoted with dashed lines. FIG. 3e, Assembled hydrogel photographs and corresponding TEM images of the KLDL (SEQ ID NO:5) (left) and KLDL (SEQ ID NO:5)$_{Linear}$ (right) SAPs. FIG. 3f, Assembled hydrogel photographs and corresponding TEM images of the KFDF (SEQ ID NO:1) (left) and KFDF (SEQ ID NO:1)$_{Linear}$ (right) SAPs. FIG. 3g, Viscoelastic measurements of storage moduli, G' (Pa), and damping factor, tanδ, for KLDL (SEQ ID NO:5) and KLDL (SEQ ID NO:5)$_{Linear}$. FIG. 3h, Viscoelastic measurements of storage moduli, G' (Pa), and damping factor, tanδ, for KFDF (SEQ ID NO:1) and KFDF (SEQ ID NO:1)$_{Linear}$. Gel capacity is defined as tanδ<1 (dashed line). CD measurements performed at 500 μM SAP in 10 mM Tris buffer, pH 7.4. (n=3 repeats) SAPs for TEM and rheology prepared at 100 μM and 15 mg/mL in 1×DPBS (pH 7.4), respectively. Rheological measurements reported for angular frequency of 2.5 rads/s. (n=3 repeats) Values are mean±SEM.

FIG. 4a, Synthetic scheme for unlabeled (route I) and labeled (route II) KLDL (SEQ ID NO:5)$_{Cyclic}$ and KFDF (SEQ ID NO:1)$_{Cyclic}$ progelators. All SAPs were cyclized under dilute conditions (500 μM) with 5 eq I$_2$ in a mixture of AcOH/MeOH/H$_2$O to create a soluble progelator. Route I uses N-terminal Fmoc-protected SAPs to improve material separation during chromatographic purification. Fmoc-removal generates the intended unlabeled progelators KLDL (SEQ ID NO:5)$_{Cyclic}$ and KFDF (SEQ ID NO:1)$_{Cyclic}$. Route II depicts the synthesis of labeled progelators through N-terminal modification with 5(6)-carboxytetramethyl rhodamine prior to cyclization. FIGS. 4b-4c, HPLC (b) monitored at 214 nm and corresponding ESI spectra (c) of Fmoc-KLDL (SEQ ID NO:5)$_{Linear}$, Fmoc-KLDL (SEQ ID NO:5)$_{Cyclic}$, and KLDL (SEQ ID NO:5)$_{Cyclic}$ (835.79 m/z, 787.76 m/z, and 1070.26 m/z, respectively) verify purity and mass of synthetic modifications to KLDL (SEQ ID NO:5) peptides. FIGS. 4d-4e, HPLC (d) monitored at 214 nm and corresponding ESI spectra (e) of Fmoc-KFDF (SEQ ID NO:1)$_{Linear}$, Fmoc-KFDF (SEQ ID NO:1)$_{Cyclic}$, and KFDF (SEQ ID NO:1)$_{Cyclic}$ (781.862 m/z, 856.17 m/z, and 1355.66 m/z, respectively) verify purity and mass of synthetic modifications to KFDF (SEQ ID NO:1) peptides. In both KLDL (SEQ ID NO:5) and KFDF (SEQ ID NO:1) systems, macrocyclization causes a slight decrease in polarity and Fmoc-deprotection increases progelator polarity FIG. 4f, KLDL (SEQ ID NO:5)$_{Linear}$ SAP macrocyclization kinetics monitored by LCMS at 214 nm reveal complete cyclization after 120 min. FIG. 4g, Absorbance spectra of unlabeled and labeled KLDL (SEQ ID NO:5) progelators ($\lambda_{max}$=565 nm for rhodamine signal). FIG. 4h, KFDF (SEQ ID NO:1)$_{Linear}$ SAP macrocyclization kinetics monitored by LCMS at 214 nm reveal complete cyclization after 120 min. FIG. 4i, Absorbance spectra of unlabeled and labeled KFDF (SEQ ID NO:1) progelators ($\lambda_{max}$=565 nm for rhodamine signal). FIG. 4j, KLDL (SEQ ID NO:5)$_{Linear}$ precursor assembles as a hydrogel (left) and the resulting KLDL (SEQ ID NO:5)$_{Cyclic}$ progelator exists a soluble solution (right). FIG. 4k, KLDL (SEQ ID NO:5)$_{Linear}$ precursor assembles as a hydrogel (left) and the resulting KLDL (SEQ ID NO:5)$_{Cyclic}$ progelator exists as a soluble solution (right).

FIGS. 5a-5c, Analysis of Rho-KLDL (SEQ ID NO:5)$_{Cyclic}$ responsiveness to MMP-9, elastase, and thermolysin. (FIG. 5a) Peptide sequence and indicated enzymatic cuts sites. FIG. 5a discloses SEQ ID NO:6. (FIG. 5b), Progelator incubated with active enzymes (left insets) shows material aggregation and settling from solution, and progelator incubated with denatured enzymes (right insets) show fully dispersed peptide solutions. Corresponding TEM images (bottom) of active enzyme cleavage products show fiber formation. (FIG. 5c), CD spectra of cleavage kinetics with thermolysin. Disappearance of signal at 204 nm (black arrow), corresponds to ring-opening. d-f, Analysis of Rho-KFDF (SEQ ID NO:1)$_{Cyclic}$ to responsiveness MMP-9, elastase, and thermolysin. (FIG. 5d) Peptide sequence and indicated enzymatic cuts sites. FIG. 5d discloses SEQ ID NO:7. (FIG. 5e), Progelator incubated with active enzymes (left insets) shows material aggregation and settling from solution, and progelator incubated with denatured enzymes (right insets) show fully dispersed peptide solutions. Corresponding TEM images (bottom) of active enzyme cleavage products show fiber formation. (FIG. 5f) CD spectra of cleavage kinetics with thermolysin. Disappearance of signal at 204 nm (black arrow), corresponds to ring-opening. CD of 500 µM progelator in 10 mM Tris buffer, pH 7.4. Enzyme cleavages performed at 1 mM progelator with 1:1000, 1:250, and 1:4500 enzyme/substrate molar ratio in 1× cleavage buffers (see Methods). Samples diluted to 100 µM for TEM.

FIG. 6a, Time course rheological analysis of progelators before and after addition of thermolysin (t=40 min). Divergence of G' from G" (G'>G") indicates formation of crosslinked hydrogel. FIGS. 6b-6c, Step-strain oscillation plots of resulting (FIG. 6b) linearized KLDL (SEQ ID NO:5) and (FIG. 6c) linearized KFDF (SEQ ID NO:1) SAP hydrogels at 9 hr post-enzyme-activation reveal repeat healing (3 min at 100% strain, 15 min at 0.1% strain, n=3 cycles). Angular frequency 2.5 rad/s, 0.1% strain. FIGS. 6d-6e, Images of (FIG. 6d) KLDL (SEQ ID NO:5)$_{Cyclic}$ and (FIG. 6e) KFDF (SEQ ID NO:1)$_{Cyclic}$ progelators in the absence (−) and presence (+) of thermolysin with corresponding TEM. Enzyme cleavages at 10 mM in 1×DPBS with 1:4500 enzyme/substrate molar ratio. TEM of samples diluted to 100 µM. FIG. 6f, CD of KFDF (SEQ ID NO:1)$_{Cyclic}$ before and after subsequent additions of thermolysin at 0.5, 1.2, 25, and 73 hr shows gradual disappearance of minimum around 204 nm from π-π* interactions between stacked cyclic peptides. 500 µM peptide in 10 mM Tris, pH 7.4. FIG. 6g, TCEP (1.2 eq) induced reduction of progelator disulfide bond shows ideal assembly of linearized progelators. Two minima at 204 nm (π→π*) and 215 nm (n→π*) reveal weak aromatic π-π* interactions and β-sheets assembly, respectively. 500 µM peptide in H$_2$O, pH 7.4.

FIG. 7a, Complex viscosity of KLDL (SEQ ID NO:5)$_{Cyclic}$ and KFDF (SEQ ID NO:1)$_{Cyclic}$ progelators reveal >20× decrease in comparison to corresponding unmodified KLDL (SEQ ID NO:5) and KFDF (SEQ ID NO:1) SAPs. FIG. 7b, Schematic illustrating catheter applicability of KLDL (SEQ ID NO:5) and KFDF (SEQ ID NO:1) SAPs vs that of enzyme-responsive KLDL (SEQ ID NO:5)$_{Cyclic}$ and KFDF (SEQ ID NO:1)$_{Cyclic}$ progelators. Injection of SAP hydrogels causes clogging. FIG. 7c, Experimental setup of progelator (2 mol % labeled) catheter injection test. Peptide was (1) loaded in a 1 mL syringe, (2) mounted on a syringe pump, and (3) flowed at 0.6 mL/min through the inner nitinol tubing (27 G) of a MyoStar transendocardial injection catheter. The catheter was (4) submerged in a circulating water bath heated to 37° C. The collection tube (5) before (top) and after (bottom) injection show successful injection. FIG. 7d, Image of KLDL (SEQ ID NO:1)$_{Cyclic}$ and KFDF (SEQ ID NO:1)$_{Cyclic}$ progelators (2 mol % labeled) after catheter injection into an empty vial (left) or a vial containing thermolysin (right), demonstrating that injection does not disrupt enzyme-responsiveness. Progelator formulated as 10 mM in 1×DPBS (pH 7.4) and treated with 1:4500 enzyme/substrate molar ratio.

FIGS. 8a-8d, Hemocompatibility analysis of progelator in human blood. FIG. 8a, Activated clotting time (ACT) in whole human blood. Collagen (pos) and blood without calcium (neg) controls. Samples without calcium exceed instrument maximum time range (>1500 sec). (n=6 per group) FIG. 8b, Whole blood hemostasis kinetics monitored at 5, 15, 30, and 45 min in recalcified human blood. Collagen (pos), glass coverslip (pos), and blood without calcium (neg) controls. (n=4 per group) FIG. 8c, Hemolysis of isolated RBCs after 1 hr incubation. 1% Triton X-100 (pos) and vehicle only (neg) normalization controls. (n=4 per group) FIG. 8d, Pro-thrombotic profile in platelet poor plasma (PPP) plotted with respect to time. Onset of coagulation is accompanied by an increase in absorbance. Collagen (pos) and no calcium (neg) controls. (n=6 per group) Vehicle in all samples contain biological fluid without progelator. Progelator concentrations are 1:20000, 1:10000, 1:5000, 1:1000, 1:500, 1:100, and 1:10 blood volume dilution of injected dosage. ns (p>0.05), *(p≤0.001), **(p≤0.0001). Ordinary one-way ANOVA for comparison with vehicle standard for FIG. 8a and FIG. 8c. Two-way ANOVA at each timepoint for comparison with vehicle standard for FIG. 8b. Values are mean±SEM. e, In vivo study timeline. Female Sprague-Dawley rats that received ischemic reperfusion surgery (35 min occlusion) were provided a single 75 µL intramyocardial injected of KFDF (SEQ ID NO:1)$_{Cyclic}$ progelator (5 mol % Rho-KFDF (SEQ ID NO:1)$_{Cyclic}$) at 7 days post-MI, to simulate a local injection. Animals were euthanized at 24 hr post-injection, and hearts were collected. Progelator formulated at 10 mM peptide in 1×DPBS (pH 7.4) (n=5 animals). FIG. 8f, H&E stained representative heart section. Selected regions at 10× magnification (right) illustrate hydrogel assembly in the infarct. Arrows point to peptide material. FIG. 8g, Fluorescence images of the neighboring section, stained for nuclei (blue) and α-actinin (green greyscales), with rhodamine-labeled peptide gels in red. LV is left ventricle. Scale bars of whole heart and zoomed in 10× magnification, 1 mm and 200 µm, respectively.

FIGS. 9a-9f, KLDL (SEQ ID NO:5) (FIG. 9a), KLDL (SEQ ID NO:5)$_{Control}$ (FIG. 9b), KLDL (SEQ ID NO:5)$_{Linear}$ (FIG. 9c), Rho-KLDL (SEQ ID NO:5)$_{Linear}$ (FIG. 9d), KLDL (SEQ ID NO:5)$_{Cyclic}$ (FIG. 9e), and Rho-KLDL (SEQ ID NO:5)$_{Cyclic}$ (FIG. 9f).

FIGS. 10a-10f, KFDF (SEQ ID NO:1) (FIG. 10a), KFDF (SEQ ID NO:1)$_{Control}$ (FIG. 10b), KFDF (SEQ ID NO:1)$_{Linear}$ (FIG. 10c), Rho-KFDF (SEQ ID NO:1)$_{Linear}$ (FIG. 10d), KFDF (SEQ ID NO:1)$_{Cyclic}$ (FIG. 10e), and Rho-KFDF (SEQ ID NO:1)$_{Cyclic}$ (FIG. 10f).

FIGS. 11a-11l, Spectra with accompanied m/z species identifications (shown in red) for unmodified SAPs, functionalized SAPs, and progelators in study. (FIG. 11a) KLDL (SEQ ID NO:5), (FIG. 11b) KFDF (SEQ ID NO:1), (FIG. 11c) KLDL (SEQ ID NO:5)$_{Control}$, (FIG. 11d) KFDF (SEQ ID NO:1)$_{Control}$, (FIG. 11e) KLDL (SEQ ID NO:5)$_{Linear}$, (FIG. 11f) KFDF (SEQ ID NO:1)$_{Linear}$, (FIG. 11g) Rho-KLDL (SEQ ID NO:5)$_{Linear}$, (FIG. 11h) Rho-KFDF (SEQ ID NO:1)$_{Linear}$, (FIG. 11i) KLDL (SEQ ID NO:5)$_{Cyclic}$, (FIG. 11j) KFDF (SEQ ID NO:1)$_{Cyclic}$, (FIG. 11k) Rho-KLDL (SEQ ID NO:5)$_{Cyclic}$, and (FIG. 11l) Rho-KFDF (SEQ ID NO:1)$_{Cyclic}$. FIG. 11m, Corresponding sequences (FIG. 11m discloses SEQ ID NOS:3, 8-11, 10-11, 6-7 and 6-7, respectively, in order of appearance) with expected molecular weight (MW) and observed m/z values. * indicates a disulfide bond between neighboring cysteines.

FIGS. 12a-12d. Morphology and rheological properties of KLDL (SEQ ID NO:5) and KFDF (SEQ ID NO:1). Unmodified linear SAP compared with respect to molar concentration (10 mM) present as porous networks hydrogel networks with rehealable properties. Stiffer gels obtained when Phe substituted for Leu in the KFDF (SEQ ID NO:1) SAP. FIGS. 12a-12b, SEM of (FIG. 12a) KLDL (SEQ ID NO:5) and (FIG. 12b) KFDF (SEQ ID NO:1) SAPs. FIG. 12c, Storage modulus (G') for KLDL (SEQ ID NO:5) and KFDF (SEQ ID NO:1) SAPs in H$_2$O or 1×DPBS show increasing stiffness with increasing saline content and peptide hydrophobicity. Angular frequency 2.5 rad/s, 0.1% strain. FIGS. 12d-12e, Step-strain oscillation analyses of (FIG. 12d) KLDL (SEQ ID NO:5) and (FIG. 12e) KFDF (SEQ ID NO:1) SAPs show rapid and repeat healing capacity of hydrogels (G'>G") following complete network disruption (G'">G') at high strains. Viscoelastic storage (G') and loss (G") moduli are plotted as a function of time with step cycles at 100% destructive strain (t=3 min) followed by 0.1% recovery strain (t=15 min) to monitor healing. Hydrogels prepared at 10 mM in 1×DPBS. Angular frequency 2.5 rad/s.

FIGS. 13a-13e, Storage (G') and loss (G") moduli were measured as a function of strain (0.5-50%) to identify the linear viscoelastic region (LVR) and appropriate rheological measurement conditions for all SAPs. Corresponding plots of (FIG. 13a) KLDL (SEQ ID NO:5), (FIG. 13b) KFDF (SEQ ID NO:1), (FIG. 13c) KFDF (SEQ ID NO:1)$_{Control}$, (FIG. 13d) KFDF (SEQ ID NO:1)$_{Linear}$, (FIG. 13e) KFDF (SEQ ID NO:1)$_{Cyclic}$+thermolysin, and (FIG. 13f) KLDL (SEQ ID NO:5)$_{Cyclic}$+thermolysin. A strain of 0.5% lies within the LVR for these strain sweeps and was chosen for all rheological measurements in this study. SAPs were prepared at 15 mg/mL in 1×DPBS. Angular frequency 2.5 rad/s.

FIGS. 14a-14b, Rho-KLDL (SEQ ID NO:5)$_{Linear}$ (FIG. 14a) and resulting cyclization product (FIG. 14b) Rho-KLDL (SEQ ID NO:5)$_{Cyclic}$. Masses are 2694.00 m/z [M+H]$^{1+}$ and 2549.46 m/z [M+H]$^{1+}$, respectively. FIGS. 14c-14d, Rho-KFDF (SEQ ID NO:1)$_{Linear}$ (FIG. 14c) and resulting cyclization product (FIG. 14d) Rho-KFDF (SEQ ID NO:1)$_{Cyclic}$. Masses are 2989.69 m/z [M+H]$^{1+}$ and 2754.18 m/z [M+H]$^{1+}$, respectively.

FIGS. 15a-15b, HRMS spectra for (FIG. 15a) KLDL (SEQ ID NO:5)$_{Cyclic}$ and (FIG. 15b) Rho-KLDL (SEQ ID NO:5)$_{Cyclic}$. FIG. 15c, Corresponding summary of theoretical m/z, measured m/z, measurement error, and elemental compositions for opened and closed conformations. FIGS. 15d-15e, HRMS spectra for (FIG. 15d) KFDF (SEQ ID NO:1)$_{Cyclic}$ and (FIG. 15e) Rho-KFDF (SEQ ID NO:1)$_{Cyclic}$. FIG. 15f, Corresponding summary of theoretical m/z, measured m/z, measurement error, and elemental compositions for opened and closed conformations. All measurements reveal closed conformation in contrast to open linear peptide.

FIG. 16a, MS$^1$ spectrum for Rho-KLDL (SEQ ID NO:5)$_{Cyclic}$ with peak identities labeled in green. FIG. 16b, Corresponding MS$^2$ fragmentation spectrum filtered for the 1276 m/z ion. Peak identities, as determined by DisConnect software, are displayed in Table 3. FIG. 16c, MS$^1$ spectrum for Rho-KLDL (SEQ ID NO:5)$_{Cyclic}$ with peak identities labeled in green. FIG. 16d, Corresponding MS$^2$ fragmentation spectrum filtered for the 1378 m/z ion. Peak identities, as determined by DisConnect software, are displayed in Table 4. Note that only normal fragmentation peaks (no H2O, NH3, or CO losses) are identified.

FIG. 17a, KFDF (SEQ ID NO:1)$_{Cyclic}$ was pre-dissolved at 10 mg/mL in H$_2$O at pH 9 and added to solvent in the DLS cuvette such that final concentrations were 1 mg/mL in H$_2$O, 1×DPBS, or 295 mM sucrose (pH 7.4). Scattering was highest for sucrose solutions and equivalent in H$_2$O and 1×DPBS after 2 hr incubation indicating smaller assemblies in the later solvent. Intensities were corrected for background solvent scattering. Scattering intensities were normalized to individual solvents. FIGS. 17b-17d, TEM analysis in H$_2$O (FIG. 17b), 1×DPBS (FIG. 17c), and 295 mM sucrose (FIG. 17d), diluted to 100 µM. Large structures were absent in H$_2$O and 1×DPBS with some small clusters of fibrils in sucrose.

FIG. 20a, Sequences of the KFDF (SEQ ID NO:1)$_{Cyclic}$ progelator cleavage reactions and KFDF (SEQ ID NO:1)$_{Linear}$ analogue for comparison. FIG. 20a discloses SEQ ID NOS 7, 12-13, 7, 14 and 7, respectively, in order of appearance. FIG. 20b, LCMS spectrum of KFDF (SEQ ID NO:1)$_{Linear}$ analogue ($R_t$=12.5 min) as a positive control. FIG. 20c, LCMS spectra of KFDF (SEQ ID NO:1)$_{Cyclic}$ progelator treated with denatured (top) and active (bottom) MMP-9 catalytic domain for 5 hr. FIG. 20d, LCMS spectra of KFDF (SEQ ID NO:1)$_{Cyclic}$ progelator treated with denatured (top) and active (bottom) porcine elastase for 5 hr. Calculated percent cleavages are reported in the spectra. Cleavage products are indicated with red asterisks. Due to the large number of cis/trans configurational isomers and amphiphilic self-assembling nature of our cyclic peptides, our pure KFDF (SEQ ID NO:1)$_{Cyclic}$ progelator eluted within an $R_t$ range between 9.7-12.5 min. Cleaved peptide peaks ($R_t$~12.4 min) have better resolution likely due to increased molecular flexibility. Cleavage reactions are described in the Methods section of the main text.

FIG. 21a, High tension (HT) voltage plot of thermolysin cleavage of Rho-KLDL (SEQ ID NO:5)$_{Cyclic}$ over time. FIG. 21b, High tension (HT) voltage plot of thermolysin cleavage of Rho-KFDF (SEQ ID NO:1)$_{Cyclic}$ over time. Detector saturation at wavelengths where HT voltage >800 mV. Peptide concentration 125 μM. [substrate:enzyme]=4500:1.

FIG. 22a, Sequences, chemical structures, and corresponding diagrammatical representations of peptides, with green denoting gelator sequence and red denoting cleaved substrate recognition sequences. FIG. 22a discloses SEQ ID NOS:8-9, respectively, in order of appearance. FIG. 22b, Predicted structures and ribbon diagrams (bottom) of KLDL (SEQ ID NO:5)$_{Control}$ and KFDF (SEQ ID NO:1)$_{Control}$ SAPs from FibPredictor simulations revealing parallel β-sheet orientations (see Supplementary Tables 1-2). FIG. 22c, Experimental circular dichroism (CD) spectra of KLDL (SEQ ID NO:5)$_{Control}$ and KFDF (SEQ ID NO:1)$_{Control}$ SAPs, with labeled minima at 215 nm (n→π*) and 203 nm (π→π*). FIG. 22d, Assembled hydrogel photographs and corresponding TEM images of KLDL (SEQ ID NO:5)$_{Control}$ (left) and KFDF (SEQ ID NO:1)$_{Control}$ (right) SAPs. FIG. 22e, Viscoelastic measurements of storage moduli, G' (Pa), and damping factor, tanδ, for KLDL (SEQ ID NO:5)$_{Control}$ and KFDF (SEQ ID NO:1)$_{Control}$. Gel capacity is defined as tanδ<1 (dashed line). CD measurements performed at 500 μM SAP in 10 mM Tris buffer, pH 7.4. (n=3 repeats) SAPs for TEM and rheology prepared at 100 μM and 15 mg/mL in 1×DPBS (pH 7.4), respectively. Rheological measurements reported for angular frequency of 2.5 rads/s. (n=3 repeats) Values are mean±SEM.

FIG. 23b, Corresponding high tension (HT) voltage plots. Concentration 500 μM progelator. (n=3 repeats).

FIGS. 26a-26. Pro-thrombotic assay statistics. Supplementary data corresponding to FIG. 8d in main text. FIG. 26a, Coagulation rate measured as the maximal first derivative, or slope, of coagulation. FIG. 26b, Time at which coagulation is at half maximal completion. FIG. 26c, Extent of coagulation measured as the plateau absorbance. (n=6 group). Progelator concentrations are 1:20000, 1:10000, 1:5000, 1:1000, 1:500, 1:100, and 1:10 volume dilution in PPP. ns (p>0.05), *(p≤0.001), **(p≤0.0001). Ordinary one-way ANOVA for comparison with vehicle standard. Values are mean±SEM.

FIG. 27a, Merged (left) and red channel-only (right) fluorescence images of 18 slices from 5 rat hearts that received intramyocardial injections of KFDF (SEQ ID NO:1)$_{Cyclic}$ progelator at 7 days post-MI and harvested 24 hr later. Images correlate with FIG. 6. Tissue is stained for myocardium with anti-α-actinin antibody (green) and nuclei with Hoechst (blue), and peptides are visualized through the rhodamine tag (red). Peptide is localized within the MI region (+blue–green). FIG. 27b, Representative slice of heart receiving saline injection at 7 days post-MI and harvested 24 hr later. Scale bar=2 mm.

DETAILED DESCRIPTION OF THE INVENTION

Figures 3A, 3B, 3C, 3D, 3E, 3F, 3G, 3H:
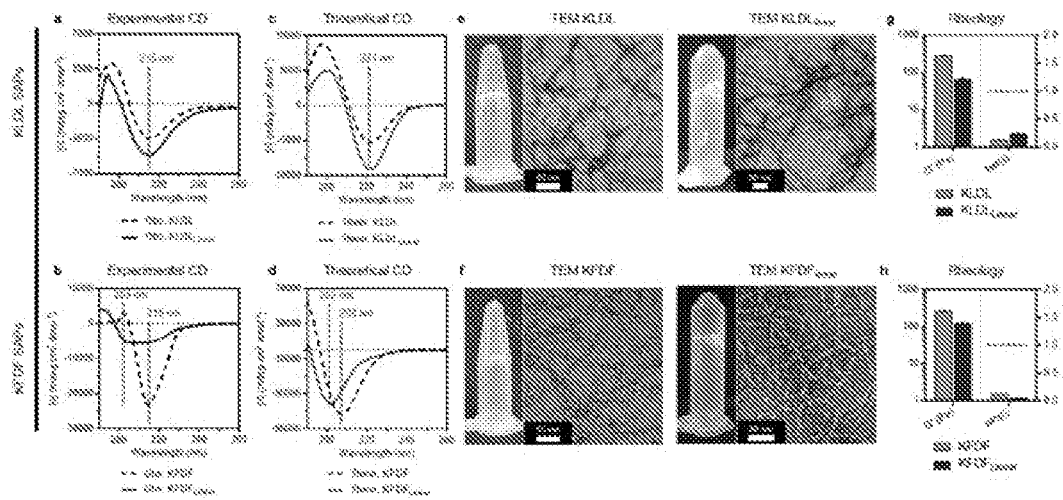
FIGS. 3a-3h. Impact of SAP functionalization on assembly properties.

All publications, patents, and patent applications mentioned in this specification are herein incorporated by reference to the same extent as if each individual publication, patent, or patent application was specifically and individually indicated to be incorporated by reference.

Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

As used herein, "patient" or "subject" means a human or animal subject to be treated.

As used herein the term "pharmaceutical composition" refers to a pharmaceutical acceptable compositions, wherein the composition comprises the peptides of the present invention, and in some embodiments further comprises a pharmaceutically acceptable carrier. In some embodiments, the pharmaceutical composition may be a combination of pharmaceutically active agents, including cells.

As used herein the term "pharmaceutically acceptable" means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

As used herein the term "pharmaceutically acceptable carrier" refers to an excipient, diluent, preservative, solubilizer, emulsifier, adjuvant, and/or vehicle with which demethylation compound(s), is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art.

As used herein, "therapeutically effective" refers to an amount of a peptide of the present invention that is sufficient to treat or ameliorate, or in some manner reduce the symptoms associated with ischemic or inflamed tissue, such as but not limited to a myocardial infarction by providing a scaffolding for tissue remodeling and/or cellular growth. When used with reference to a method, the method is sufficiently effective to treat or ameliorate, or in some manner reduce the symptoms associated with ischemia. For example, an effective amount in reference to myocardial infarction is that amount which is sufficient to palliate, ameliorate, stabilize, reverse or slow progression of the disease, or otherwise reduce pathological consequences of the disease. In any case, an effective amount may be given in single or divided doses.

As used herein, the term "treatment" including co-administration with other pharmaceutically active agents (e.g., cells) embraces at least an amelioration of the symptoms associated with ischemic conditions in the patient, where amelioration is used in a broad sense to refer to at least a reduction in the magnitude of a parameter, e.g. a symptom associated with the disease or condition being treated. As such, "treatment" also includes situations where the disease, disorder, or pathological condition, or at least symptoms associated therewith, are completely inhibited (e.g. prevented from happening) or stopped (e.g. terminated) such that the patient no longer suffers from the condition, or at least the symptoms that characterize the condition, due at least in part to the administration of the present compositions.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, 22th ed., (Pharmaceutical Press and Philadelphia College of Pharmacy at University of the Sciences 2012).

The invention provides a tissue scaffolding composition and method of use for treating tissues in need thereof, e.g., ischematic tissue in myocardial infarctions, comprising in various embodiments a cyclic peptide. In embodiments, the cyclic peptide comprises a substrate recognition sequence that when enzymatically cleaved linearizes and self assembles the peptide with like-kind peptides, e.g., via beta-sheets, into a hydrogel.

In embodiments, the peptide has at least one, preferably three or more, repeating amino acid sequence KFDF (SEQ ID NO:1) or KLDL (SEQ ID NO:5) or other known self-assembling peptide (SAP) gelling sequences. Another exemplary peptide gelling sequence that forms a hydrogel via self-assembly is QQFEWEFEQQ (SEQ ID NO:108). The invention provides cyclic peptides that can self-assemble into a hydrogel when enzymatically cleaved, such as via beta-sheets, (EAK16, RADA16-I, RADA16-II, and Rpl1) alpha-helices (hSAFaaa and other two-component systems based on coiled-coil heptad sequence repeats, abcdefg) or beta-hairpins (MAX1 and MAX8), that further assemble viscoelastic hydrogels. Well-known SAPs are described in the literature, and incorporated by reference herein, for example: Sun et al., "Self-Assembled Peptide Nanomaterials for Biomedical Applications: Promises and Pitfalls," International Journal of Nanomedicine, 2016, 12:73-86; Habibi et al., "Self-Assembled Peptide-Based Nanostructures: Smart Nanomaterials Toward Targeted Drug Delivery," Nanotoday, 2016, 11(1):41-60; Eskandari et al., "Recent Advances in Self-Assembled Peptides: Implications for Targeted Drug Delivery and Vaccine Engineering," Advanced Drug Delivery Reviews, 2017, 110-111:169-187; and Banwell et al., "Rational Design and Application of Responsive α-Helical Peptide Hydrogels," Nature Materials, 2009, 8:596-600.

In embodiments, the peptide is cyclized by disulfide bonds on cysteine residues, but other functional moieties and chemistries can be used to cyclize the peptides. In embodiments, the substrate recognition sequence is specific for inflammatory-related enzymes, matrix metalloproteinases (MMP)-2/9 and/or elastase. In embodiments, the peptide sequence comprises a MMP-2/9 cleavable sequence PLGLAG (SEQ ID NO:2). Cleavage in situ allows assembly of the gelling sequence into a hydrogel. In embodiments, the peptide comprises or consists essentially of the amino acid sequence CKFDFKFDFKFDFPLGLAGC (SEQ ID NO:7). In embodiments, the peptide is labeled for detection. In alternative embodiments, the composition further comprises a therapeutic agent (including small molecules, biologics and cells), a chemotactic agent, an antibiotic, and/or a growth factor.

The invention provides a method of creating a scaffold for tissue repair in a patient in need thereof comprising administering to the patient a tissue scaffolding composition as described. In embodiments, the scaffold is used in treating inflamed ischemic or damaged tissue, for example in negative left ventricular remodeling post-myocardial infarction. In embodiments, the administration is via a catheter, parenteral injection, or implantation.

In certain embodiments, the present invention provides compositions and methods comprising injecting or implanting in a subject in need an effective amount of the tissue scaffolding composition. The composition can further comprise cells, drugs, proteins, or polysaccharides. The composition can be delivered as a liquid, and can transition to a gel form after delivery and in situ enzymatic cleavage. In some instances, the composition is coated on a device such as an implant.

In some instances the composition comprises cells, proteins, or therapeutic agents. In some instances, the composition further comprises non-naturally occurring factors that recruit cells into the composition, encourage growth or prevent infection. In some instances, the composition further comprises a therapeutic agent, and as such is configured as a drug delivery vehicle.

In some instances, the composition herein can recruit endogenous cells within the recipient and can coordinate the function of the newly recruited or added cells, such as stem cells, allowing for cell proliferation or migration within the composition. A composition herein can further comprise one or more additional components, for example without limitation: an exogenous cell, a peptide, polypeptide, or protein, a vector expressing a DNA of a bioactive molecule, and other therapeutic agents such as drugs, cellular growth factors, nutrients, antibiotics or other bioactive molecules.

The composition of the invention can further comprise cells, drugs, proteins, or other biological material such as, but not limited to, erythropoietin (EPO), stem cell factor (SCF), vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factor (CGF), stem cell factor (SCF), platelet-derived growth factor (PDGF), endothelial cell growth supplement (EGGS), colony stimulating factor (CSF), growth differentiation factor (GDF), integrin modulating factor (IMF), calmodulin (CaM), thymidinc kinase (TK), tumor necrosis factor (TNF), growth hormone (GH), bone morphogenic proteins (BMP), tissue inhibitor matrix metalloproteinase (TIMP), interferon, interleukins, cytokines, integrin, collagen, fibrillins, fibronectin, laminin, glycosaminoglycans, hemonectin, thrombospondin, heparan sulfate, dermantan, chondroitin sulfate (CS), hyaluronic acid (HA), vitronectin, proteoglycans, transferrin, cytotactin, tenascin, and lymphokines.

In some instances, the composition can comprise a biological group that can act as an adhesive or anchor where the composition is delivered. In one instance, a composition can be a bioadhesive, for example, for wound repair. In some instances, a composition herein can be configured as a cell adherent. For example, the composition herein can be coating or mixed with on a medical device or a biologic that does or does not comprises cells. For example, the composition herein can be a coating for a synthetic polymer graft. In some instances, the composition includes an anti-bacterial or anti-bacterial agents. Methods herein can comprise delivering the composition as a wound repair device.

In embodiments, the invention utilizes a cyclic peptide pro-gelator which is soluble and nonviscous in buffered saline and self-assembles into a macromolecular hydrogel at the site of tissue injury, such as myocardial infarction (MI). Upon linearization through peptide cleavage by enzymes upregulated at the site of MI, rapid self-assembly creates a macromolecular network (millimeter scale) which traps itself into the tissue it is activated and enhances tissue retention over that of unimers or nano-scale materials. These biomaterials act to viscoelasatically mimick and supplement the supportive native extracellular matrix (ECM) that MMP-2/9 degrade following myocardial infarction. Supplementation of the degradaded ECM with a synthetic biopolymer pro-gelator enables targeted accumulation of a viscoelastic network and minimally invasive delivery to heart tissue post-MI.

Low viscosity makes this material not only injectable, but amenable to tranendocardial catheterization and catheter-based coronary infusion, a characteristic which has only been demonstrated with three other materials: decellularized myocardial ECM hydrogel, aliginate hydrogel, and oxime cross-linked hydrogel. This allows for minimally invasive and local delivery to the heart tissue. In contrast, known promising hydrogel-based biomaterials require invasive delivery as a patch or direct epicardial injection into compromised tissue, a quality that is not feasible for clinical application.

As coronary infusion of the prior art is known to be limited by inefficient spreading, materials which are amenable to catheterization may still not reach their intended target (infarct). Additionally, the risk of embolization is a current concern due to the propensity for injected materials to leak into the LV chamber with transendocaridal catheterization. The material of the invention is inert in the cyclic confirmation and only gels when linearized, thus making these peptides selective to areas with excess inflammation where protease activity is upregulated, in particular, that of MMP-2/9. Furthermore, the material resists gelation in serum and healthy myocardial tissue. This prevents off-target accumulation and reduces the risk of potential gelling in the blood stream.

In contrast to covalently crosslinked hydrogels in pre-clinical studies, these materials exhibit repeat healing properties (useful in an organ constantly in motion) and rheological stiffnesses similar to that found in native ECM.

As the ECM is an important hydrogel network in tissue, providing structural support and a niche for biochemical signaling and cellular infiltration, biomaterial hydrogels are being used as ECM mimicks in the wake of enzymatic degradation post-MI. Currently, there are no clinically approved hydrogel based materials for treating MI, primarily due to delivery and formulation limitations stated above. However, clinical trials using aliginate (phase II) and decellularized myocardial ECM hydrogel (phase I) delivered via catheter-based intracoronary infusion and transendocaridal catheter delivery, respectively, are currently underway.

There are currently no known stimuli responsive or catheter deliverable peptide-based formulations reported in pre-clinical studies. Pre-clinical studies with RAD16-II peptide nanofibers have only utilized direct epicardial injection either as formulations with scaffold itself or in conjunction with stem cells and growth factors (VEGF). Thus only invasive delivery techniques are being explored with peptide-based systems, potentially due to excess viscosity of the scaffold formulations.

In embodiments, these peptides are primarily composed of an amphipathic peptide sequence characterized by three repeats of Lys-Phe-Asp-Phe (SEQ ID NO:1), (KFDF)$_3$ (SEQ ID NO:4), or more, which self assemble by stacking as beta-sheets through electrostatic and hydrophobic interactions. The macromolecular hydrogel it forms is porous, elastic, and rehealable upon disruption, similar to native ECM. Modification of this gelator sequence with a matrix metalloproteinase (MMP)-2/9 cleavable sequence (e.g., PLGLAG (SEQ ID NO:2)) enables infarct-specific activation. Macrocyclization through covalent disulfide bonds on N- and C-terminal cysteine residues sterically constrains the peptide, preventing beta-sheet assembly as a hydrogel, thus affording a pro-gelator.

Further, in embodiments, this material is highly modular, in that small molecules (e.g. dyes, contrast agents, and drugs) can easily be incorporated on the N-terminal amine and used in mixed formulations of tagged and untagged peptide (in vitro enzyme cleavage using 100% rhodamine labeled peptide, and in vivo studies using 5% rhodamine labeling). Together, these modifications provide a novel way of delivering biosynthetic tissue scaffolds to diseased tissue in a minimally invasive (catheterization) and targeted (enzyme-responsive) manner.

EXAMPLES

In embodiments, the invention provides compositions and methods of use comprising a cyclic peptide progelator that flows freely in solution and resists assembly into hydrogel until acted upon by an endogenous signal (FIGS. 1a-1c), namely MMP-2/9[2,31] and elastase,[32,33] which are expressed at the site of MI during the acute inflammatory (days) and fibrotic (weeks) phases. These enzymes play key roles in the healing process through degradation of extracellular matrix (ECM) and fibrinogen.[2]

SAP sequences were prepared as water soluble, dispersed cyclic progelators (FIG. 1a) that contain a substrate recognition sequence for MMP-2/9 and elastase (red). Two different cyclic progelators were prepared; one without a fluorescent label and one with a rhodamine label (pink ellipse) located adjacent to the substrate sequence. The data shows that enzymatic cleavage of these sterically constrained cyclic progelators results in linearization to generate SAPs (FIG. 1b) which subsequently assemble into rehealable viscoelastic hydrogels (FIG. 1c). Their low viscosity, ability to gel at the site of MI, and hemocompatible nature of the concentrated progelator are demonstrated. In addition, the data shows that the progelators are amenable to minimally invasive catheter injection using an in vitro model system. This enables the delivery of SAPs to the heart via catheter.

Design of stimuli-responsive SAPs for activatable gelation in vivo. SAPs undergo spontaneous assembly through electrostatic and amphiphilic interactions into ordered nanostructures.[34,35] In many instances, variation of sequence and charge distribution in SAPs can influence properties such as secondary structure,[36] fiber diameter,[37] and bulk viscoelasticity[38]. The present invention began with a gellable core based on a SAP consisting of the repeat sequence (KLDL)$_3$ (SEQ ID NO:3) (referred to in this study as KLDL (SEQ ID NO:5)), which has been studied as a non-immunogenic, nonhemolytic, and antimicrobial scaffold for tissue engineering applications.[39-41] This peptide self-assembles spontaneously into β-sheets through cationic and anionic cross-linking of the Lys and Asp residues and hydrophobic interactions along the Leu residues. As a proof-of-concept for sequence control, an analogue of KLDL (SEQ ID NO:5) was chosen to alter secondary structural assembly and achieve modified gel properties. For this purpose, (KFDF)$_3$ (SEQ ID NO:4) (referred to as KFDF (SEQ ID NO:1)) was designed, in which the incorporation of aromatic Phe residues introduce 7-7 interactions. From the KLDL (SEQ ID NO:5) and KFDF (SEQ ID NO:1) SAPs, a small library of functionalized SAPs and progelators was engineered for studying assembly within a biological relevant environment (FIGS. 2a-2c and FIGS. 9a-11). We first evaluated whether the addition of non-gelling amino acids from the MMP-2/9 recognition sequence (PLGILAG) (SEQ ID NO:2) and cysteine residues used for macrocyclization into the SAP sequences would interfere with their ability to self-assemble (FIG. 2a). Predictive computational modeling with open-access FibPredictor software[42] provided initial evidence that functionalized KLDL (SEQ ID NO:5)$_{Linear}$ and KFDF (SEQ ID NO:1)$_{Linear}$ SAPs would experience a switch in self-assembly orientation from antiparallel to parallel β-sheets. Regardless, such a design would retain the capacity to form fibrillar bilayers (FIGS. 2b-c and Tables 1-2). Notably in KFDF (SEQ ID NO:1)$_{Linear}$, Phe residues on each strand are sandwiched with analogous residues on neighboring strands, which facilitate R-7 stacking and stronger hydrophobic interactions than those of Leu-containing peptides. Indeed, with the design validated in silico, synthetic preparation of the KFDF (SEQ ID NO:1) SAP resulted in materials with increased mechanical strength without sacrificing re-healing capacity or fibrous morphology, inherent to the known KLDL (SEQ ID NO:5) system[43] (FIGS. 12a-12d).

In practice, modified SAPs capable of going on to form the cyclic progelators, namely KLDL (SEQ ID NO:5)$_{Linear}$ and KFDF (SEQ ID NO:1)$_{Linear}$, retained the capacity to self-assemble (both experimentally and predicted) despite modest changes in secondary structure and viscoelastic properties (FIGS. 3a-3h). Experimental CD demonstrated that KLDL (SEQ ID NO:5)$_{Linear}$ and KFDF (SEQ ID NO:1)$_{Linear}$ retained (3-sheet conformations (n→π* transition at 215 nm). However, the positive peak at ~200 nm (π→π* transition) found in KLDL (SEQ ID NO:5) and KFDF (SEQ ID NO:1) is blue-shifted to −195 nm, indicative of a parallel to antiparallel orientation switch (FIG. 3a-3b).[44] Additionally, KFDF (SEQ ID NO:1)$_{Linear}$ reveals a new high energy minimum at 203 nm corresponding to π-π* effects resulting from aromatic 7-7 interactions in the hydrophobic interior of the bilayer structure (FIG. 3b).[27] This transition is predicted in theoretical spectra from DichroCalc[45] for KFDF (SEQ ID NO:1)$_{Linear}$ (202 nm) and not for KLDL (SEQ ID NO:5)$_{Linear}$, which contains no aromatic residues. (FIG. 3c-3d). Regardless of altered secondary structure, fiber morphology and bulk viscoelastic properties exhibited minimal changes to that of unmodified KLDL (SEQ ID NO:5) and KFDF (SEQ ID NO:1) (FIG. 3e-3h). Slight drops in storage moduli for KLDL (SEQ ID NO:5)$_{Linear}$ and KFDF (SEQ ID NO:1)$_{Linear}$ are attributed to the decreasing molar concentration of amino acids (hydrogels prepared with respect to weight at 15 mg/mL) contributing to β-sheet formation. Regardless, no significant disruptive effects to gelling capacity, as defined by tanδ<1 (FIG. 3g-3h) or strain tolerance (FIGS. 13a-13f) were observed through the introduction of over 66% more amino acid residues to the SAP sequence. This exemplifies the robustness of these linear SAPs to sequence modification and potential capacity to tolerate functional moieties such as fluorescent tags or small molecule drugs.

Figures 4A, 4B, 4C, 4D, 4E, 4F, 4G, 4H, 4I, 4J, 4K:
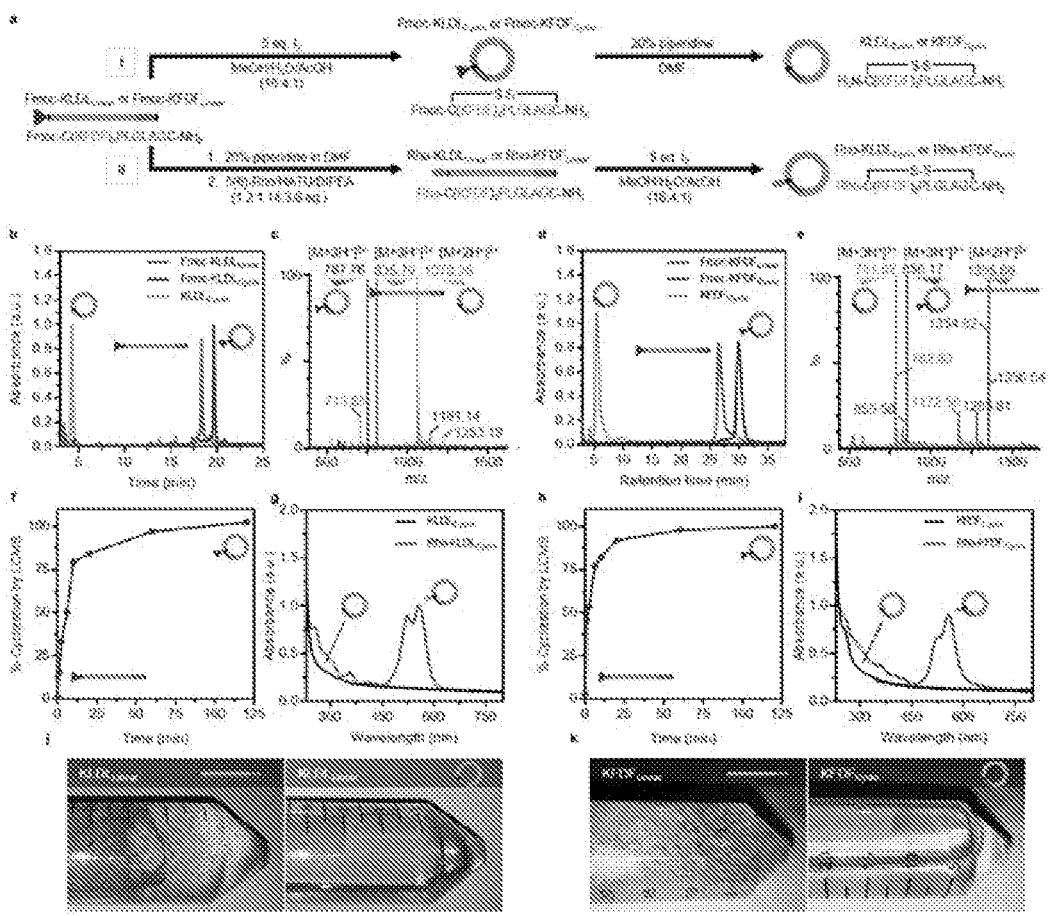
FIGS. 4a-4k. Facile synthesis of sterically constrained and labeled cyclic progelators.
Figures 17A, 17B, 17C, 17D:
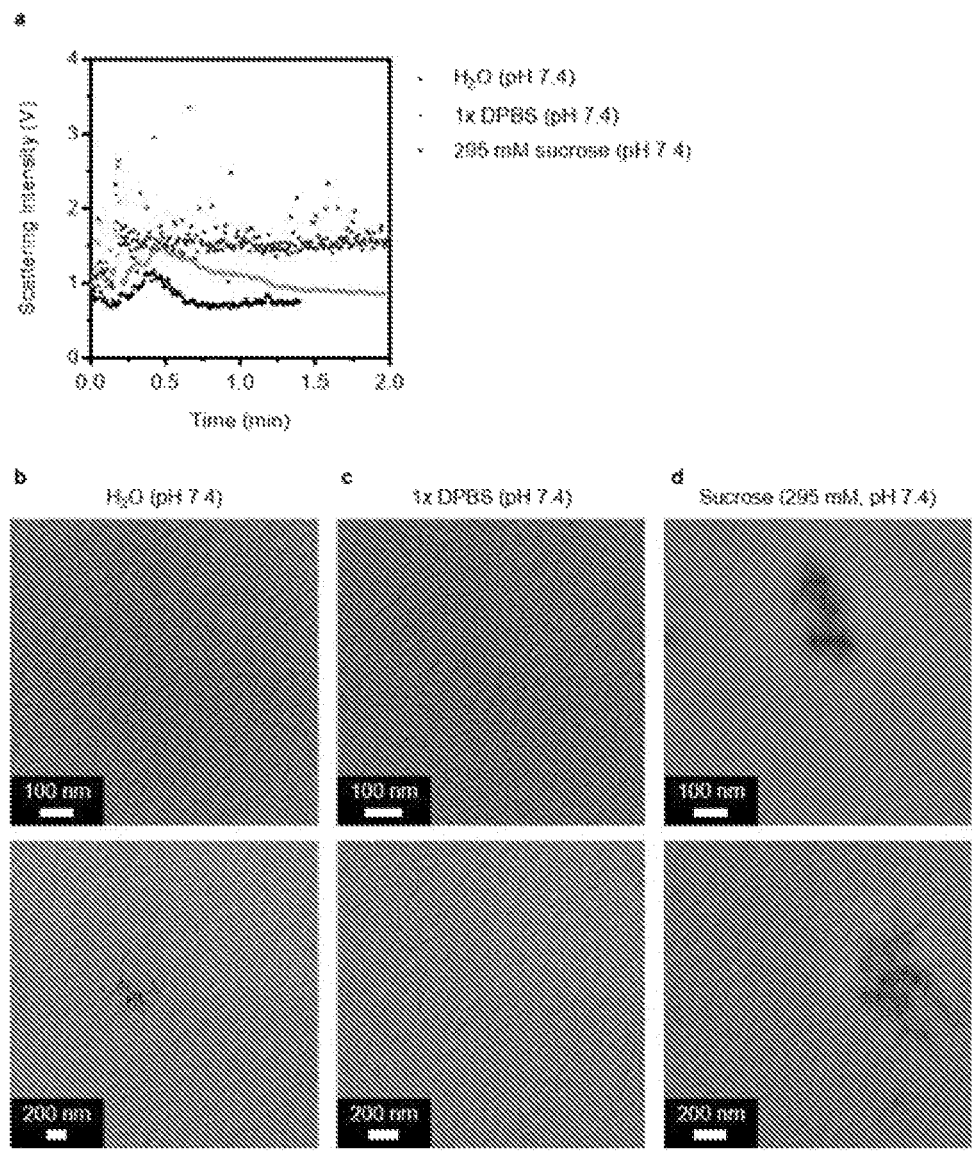
FIGS. 17a-17d. SLS profiles for unlabeled progelator in different buffers. Solutions of KFDF (SEQ ID NO:1)$_{Cyclic}$ were formulated in solvents commonly used for formulating SAPs to identify optimal solvents that minimize the occurrence of large assemblies in solution.
Figures 18A, 18B, 18C, 18D, 18E:
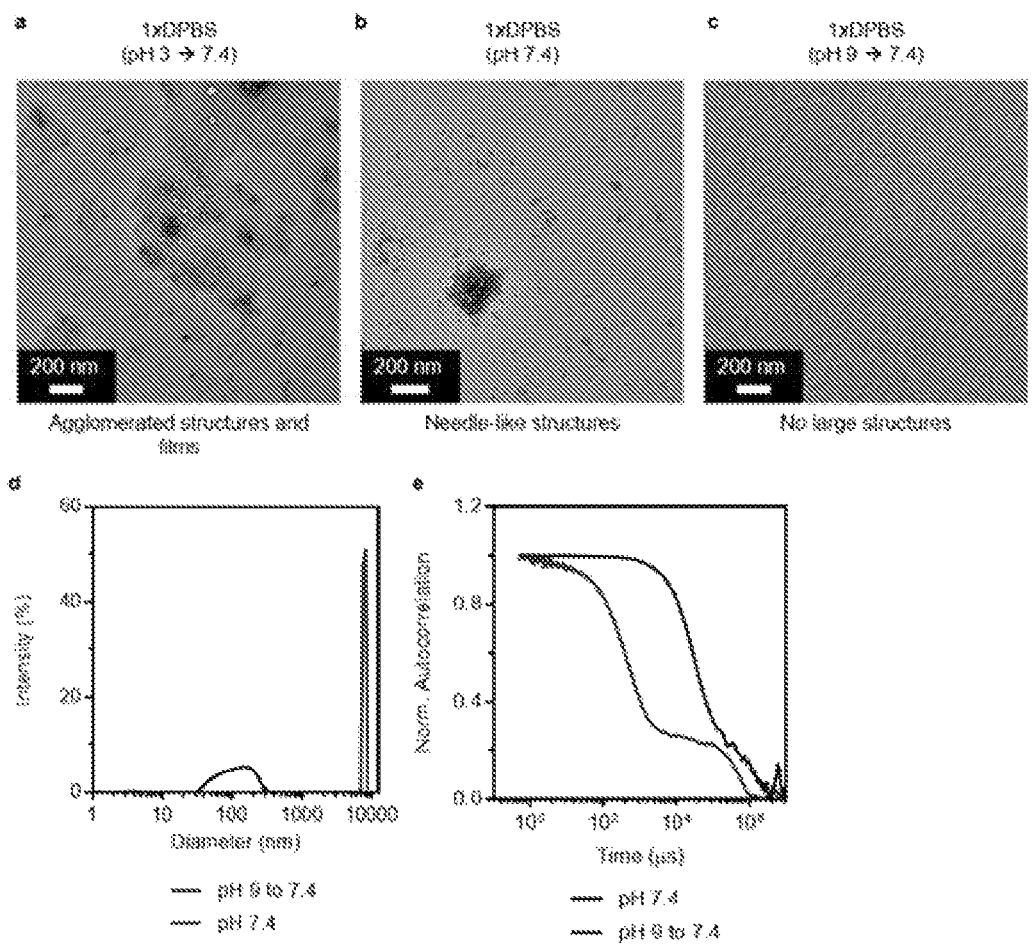
FIGS. 18a-18e. Effect of cyclic peptide progelator formulation on aggregation. Solutions of KFDF (SEQ ID NO:1)$_{Cyclic}$ and KFDF (SEQ ID NO:1)$_{Linear}$ (data not shown) were optimally formulated in 1×DPBS using a pH switch from basic (pH 9.0) to neutral (pH 7.4) conditions prior to addition of saline to limit aggregation. These formulations in 1×DPBS are stable over prolonged incubation periods (up to 3 days) under dilute (100 µM) and concentrated (10 mM) conditions. a-c, TEM (100 µM) micrographs of progelator formulated in 1×DPBS after solvent switch from acidic to neutral pH (FIG. 18a), no pH switch (FIG. 18b), or switch from basic to neutral pH (FIG. 18c). d-e, DLS (1 mg/mL) (FIG. 18d) and the corresponding normalized autocorrelation functions (FIG. 18e) depict the influence of different formulation conditions on aggregation.
Figure 19:
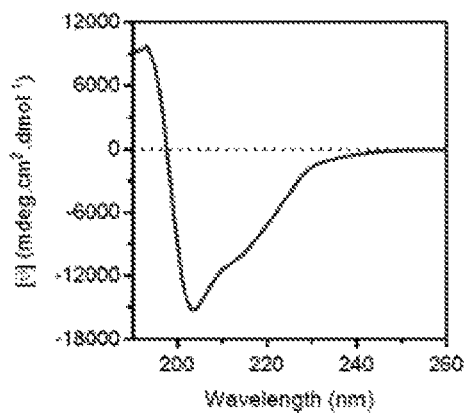
FIG. 19. Circular dichroism (CD) of KFDF (SEQ ID NO:1)$_{Cyclic}$ progelator. a, CD spectrum of KFDF (SEQ ID NO:1)$_{Cyclic}$ progelator (500 μM, pH 7.4) formulated with basic to neutral pH solvent switch. (n=3 repeats). The magnitude of the high energy minimum at 204 nm is increased significantly following cyclization of KFDF (SEQ ID NO:1)$_{Linear}$ (FIG. 2b in main text), which is attributed to aromatic π-π* effects achieved through vertically stacked macrocycles.
Figures 20A, 20B, 20C, 20D:
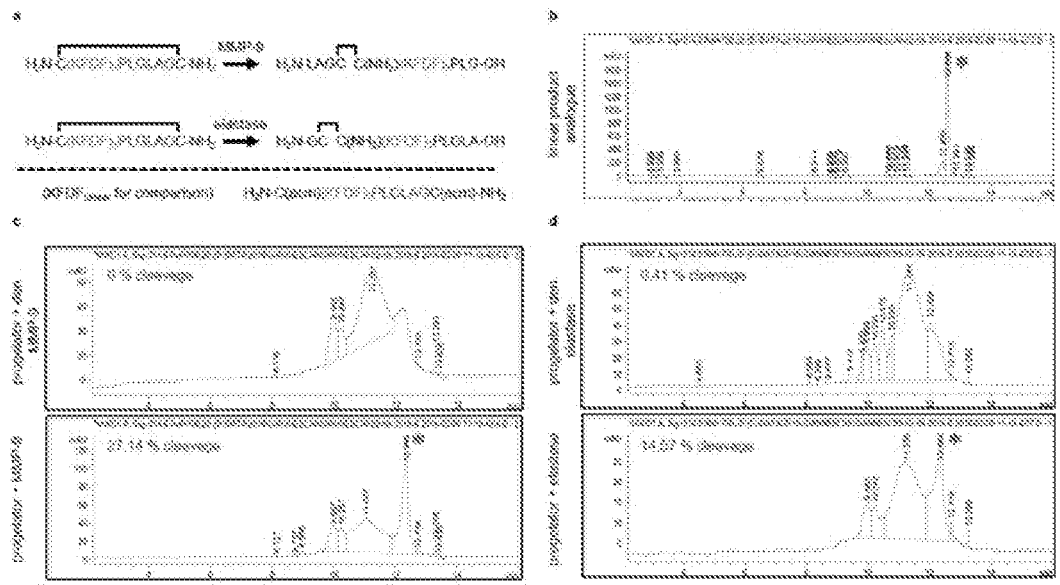
FIGS. 20a-20d. Representative enzyme cleavage of unlabeled cyclic progelator. KFDF (SEQ ID NO:1)$_{Cyclic}$ and KLDL (SEQ ID NO:5)$_{Cyclic}$ (data not shown) were treated with MI-associated enzymes, MMP-9 and elastase to confirm enzyme responsiveness.
Figures 21A, 21B:
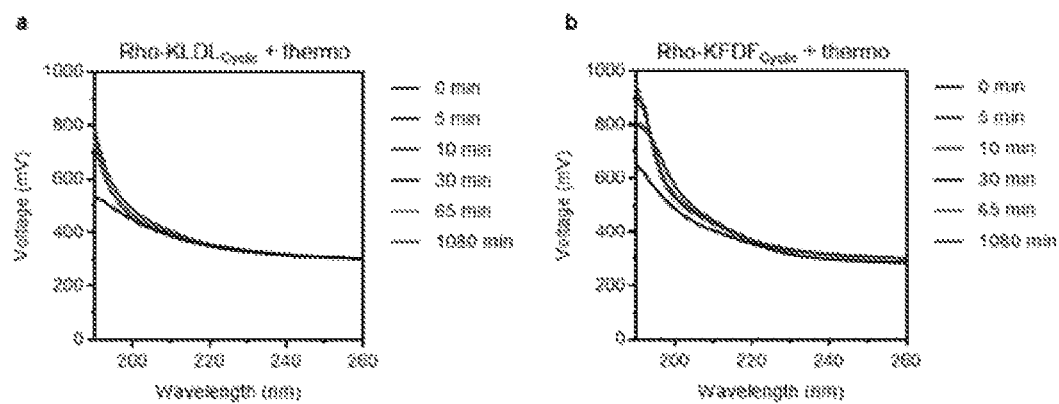
FIGS. 21a-21b. Voltage plots for thermolysin cleavage of labeled progelators by CD. Corresponding data for FIG. 5c, 5f CD spectra of time-course analysis of thermolysin cleavage.
Figures 22A, 22B, 22C, 22D, 22E:
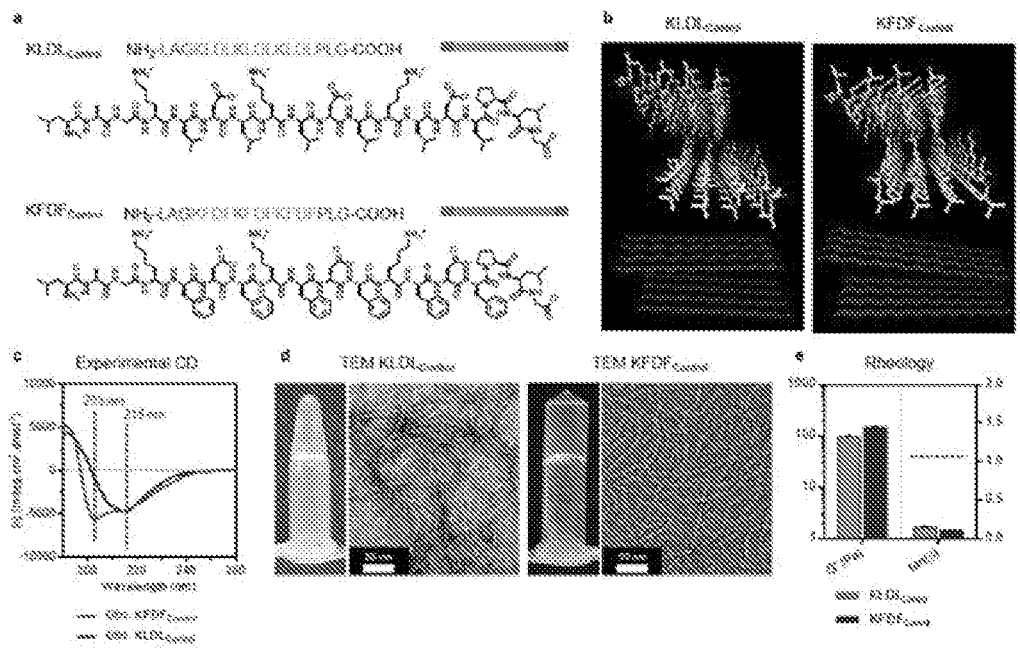
FIGS. 22a-22e. Simulated control SAPs, KLDL (SEQ ID NO:5)$_{Control}$ and KFDF (SEQ ID NO:1)$_{Control}$, from progelator cleavage. KLDL (SEQ ID NO:5)$_{Control}$ and KFDF (SEQ ID NO:1)$_{Control}$ SAPs were used to represent the enzymatically cleaved progelators containing flanking substrate residues on the gelling sequences.

Cyclization and progelator formulation. SAP steric constraint provides a simple and versatile engineering approach for preventing network assembly in a biological environment (FIGS. 4a-4k). Functionalized SAP analogues containing an Fmoc protecting group or rhodamine dye on the N-terminus were cyclized through oxidation of terminal cysteine residues to generate unlabeled and labeled progelators (FIG. 4a). Fmoc was temporarily used for unlabeled progelators to improve peak separation during purification and to monitor cyclization by HPLC and ESI (FIG. 4b-4e). Dilute solution phase macrocyclization was complete within 125 min by LCMS (FIG. 4f, 4h). Combined, MALDI, HRMS and Tandem-MS confirm synthesis of the cyclic products (FIGS. 14a-16d and Tables 3-4). UV spectra confirm the presence of rhodamine absorbance in Rho-KLDL (SEQ ID NO:5)$_{Cyclic}$ and Rho-KFDF (SEQ ID NO:1)$_{Cyclic}$ progelators (FIG. 4g, 4i). Nonviscous progelators (FIG. 4j-4k) were dialyzed into milliQ H$_2$O, sterile filtered (0.2 µm PES), and lyophilized for storage prior to use in vitro and in vivo. To ensure synthetic reproducibility and appropriate biological analysis in this study, our cyclic progelators were structurally characterized and formulated by first dissolving in aqueous solution under basic conditions, followed by neutralization to give final solutions in 1×DPBS, pH 7.4 (10 mM peptide). This formulation was determined by searching for conditions that minimized aggregation in different solvents and pH values as determined by light scattering and TEM (FIGS. 17a-18). Conformational rigidification via macrocyclization is suspected to have induced limited oligomerization via intermolecular stacking of cyclic constructs into transient nanotubes (FIG. 19), as has been reported in the literature.[46-48] Despite these observed secondary structural characteristics, large structures were absent by TEM (FIGS. 18a-18e). Thus, our formulated cyclic progelators persist as free-flowing solutions for easy injection in vivo.

Figures 5A, 5B, 5C, 5D, 5E, 5F:
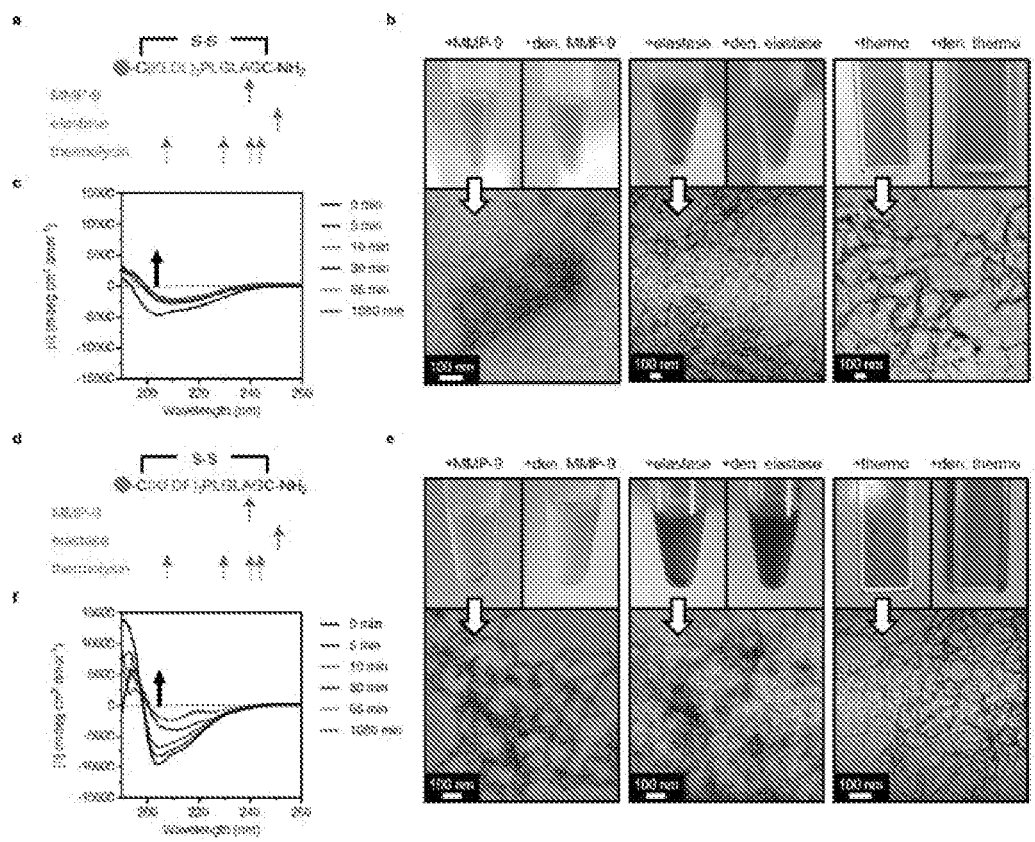
FIGS. 5a-5f. Enzyme responsiveness of Rho-KLDL (SEQ ID NO:5)$_{Cyclic}$ and Rho-KFDF (SEQ ID NO:1)$_{Cyclic}$ progelators.

Cyclic progelators are responsive to inflammation associated enzymes. Labeled cyclic peptide progelators were tested for their responsiveness to inflammatory-related proteases overexpressed post-MI (FIGS. 5a-5f). The initial inflammatory response is marked by the recruitment of abundant neutrophils, which contribute to the release of proteases such as matrix metalloproteinases (MMPs) and elastase in the first days post-MI.[31,49] The fibrotic phase (weeks post-MI) is notable for residually high MMP concentrations[2,31] and elevated sources of elastase from neutrophil extracellular traps (NETs), remaining weeks after neutrophil apoptosis.[32,33] Rho-KLDL (SEQ ID NO:5)$_{Cyclic}$, and Rho-KFDF (SEQ ID NO:1)$_{Cyclic}$ were incubated with MMP-9 catalytic domain and porcine elastase to cleave at preferential cut sites (FIGS. 5a, 5d). Enzymatic cleavage by active MMP-9 and elastase (FIGS. 20a-20d) induced visible aggregation in the reaction vial and entangled fibrous meshes by TEM, whereas denatured enzymes elicited no response (FIGS. 5b, 5e). At the site of MI, the presence of very high MMP and elastase concentrations is expected to induce rapid cleavage, forcing the peptide progelator to assemble and solidify at the target site. However, other inflammation-associated enzymes or constitutively expressed extracellular proteases could play a role in non-specific degradation. Thus, thermolysin was used as a robust nonspecific enzyme to assess general stability of our material to excess proteolysis and subsequent hydrogel disassembly in vivo.[51] Despite the promiscuous activity of thermolysin, incubation with Rho-KLDL (SEQ ID NO:5)$_{Cyclic}$ and Rho-KFDF (SEQ ID NO:1)$_{Cyclic}$ induced fiber formation by TEM (FIGS. 5b, 5e). CD revealed structural rearrangements during this linearization process (FIGS. 5c, 5f and FIGS. 21a-21b). The similar responsiveness of both unlabeled progelators to inflammatory enzymes and resistance to dissolution by thermolysin demonstrate the versatility of our conformational control strategy.

Figures 6A, 6B, 6C, 6D, 6E, 6F, 6G:
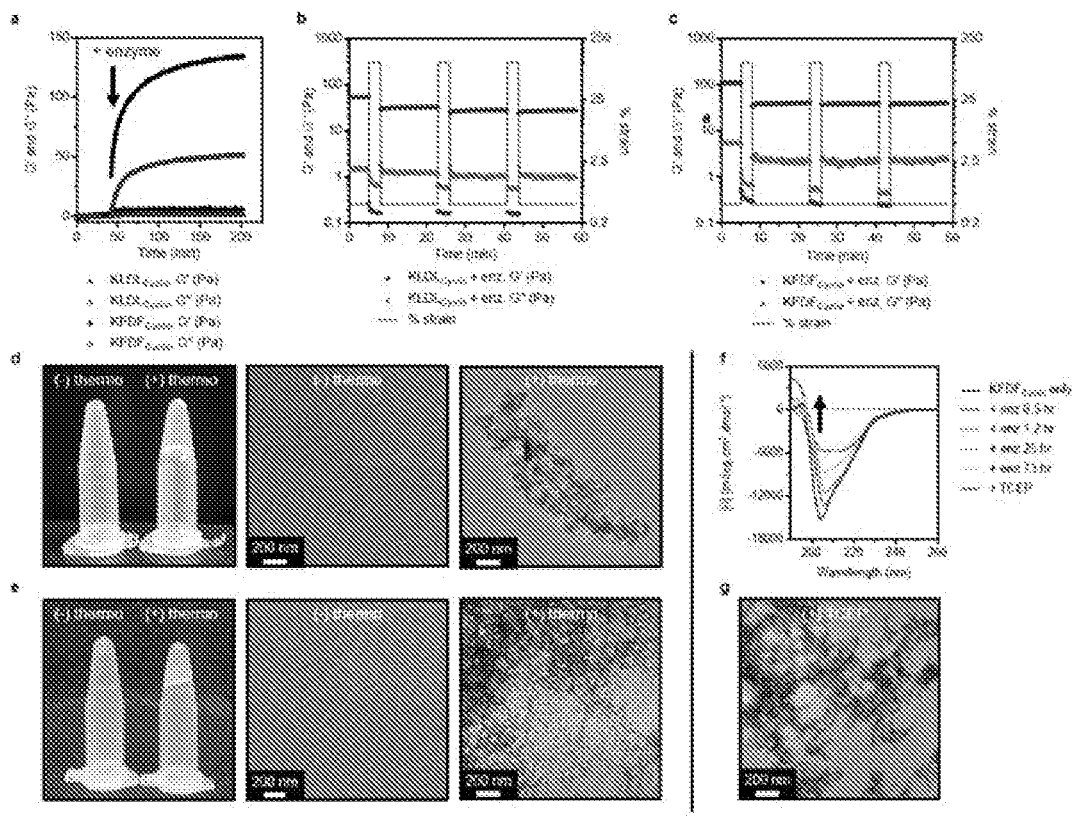
FIGS. 6a-6g. Bulk Scale Gelation of Unlabeled Cyclic Progelators.

Progelators assemble as viscoelastic and rehealable hydrogels despite robust proteolysis. The concept behind our cyclic peptide progelators is that upregulated enzymes will initiate assembly and ultimately viscoelastic gel formation at the site of MI. However, this location contains a soup of robust proteases involved in the degradation of peptides and proteins. Thus, excess proteolysis in vivo may prevent gelation or retention of hydrogels at the site of MI. To simulate this environment, we treated our material with a large quantity of the robust and nonspecific enzyme, thermolysin. Hydrogel assembly kinetics and resulting mechanical properties were then measured rheologically (FIGS. 6a-6g). Initially, KLDL (SEQ ID NO:5)$_{Cyclic}$ and KFDF (SEQ ID NO:1)$_{Cyclic}$ progelators formulated as non-viscous liquids displayed overlapping G' and G", indicative of free-flowing solutions lacking significant crosslinks or chemical interactions (FIG. 6a). Upon incubation with thermolysin, a gradual increase in G' and divergence from G" shows the formation of viscoelastic hydrogels. A steady state was reached at 200 min and continuous measurement of both shear moduli revealed no change for up to 3 days in the presence of thermolysin. The tightly entangled macromolecular scaffolds are suspected to confer some degree of resistance to further proteolysis. Furthermore, the resulting gels displayed rapid healing capacity when subjected to repeat cycles of excess strain (100%) (FIG. 6b-6c). Resulting bulk scale hydrogels and dilute TEM images of fiber assemblies from the rheometer are depicted in FIG. 6d-6e. Synthetic product analogue SAPs in which the gelator sequence contained flanking substrate residues (KLDL (SEQ ID NO:5)$_{Control}$ and KFDF (SEQ ID NO:1)$_{Control}$) were used for simple comparison with enzyme-induced gelation (FIGS. 22a-22e). Indeed, secondary assembly characteristics (CD), fibril morphology (TEM), and viscoelastic properties (rheology) of KFDF (SEQ ID NO:1)$_{Control}$ match closely to that of enzymatically cleaved KFDF (SEQ ID NO:1)$_{Cyclic}$ in FIGS. 6a-6g. However, KLDL (SEQ ID NO:5)$_{Control}$ SAP produced a viscoelastically stronger gel than that demonstrated by KLDL (SEQ ID NO:5)$_{Cyclic}$ following enzyme directed linearization.

Figures 23A, 23B:
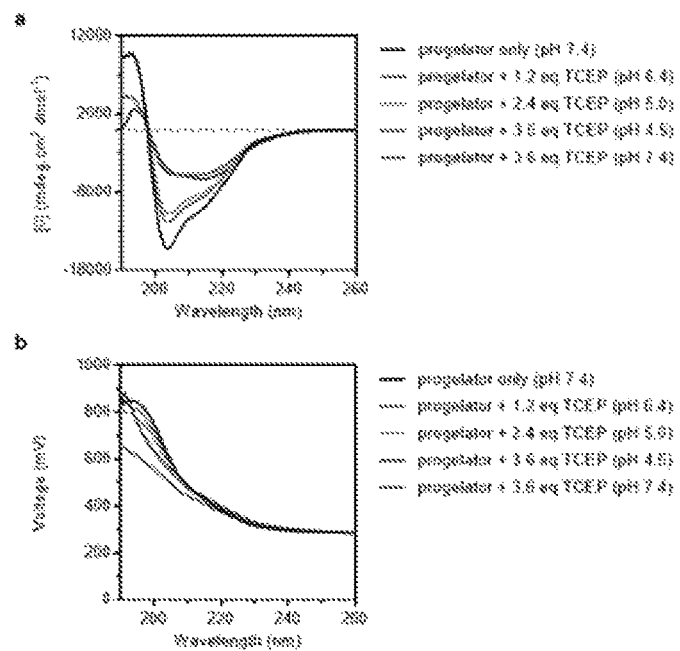
FIGS. 23a-23b. TCEP reduction of progelator. TCEP reduction indicates ideal assemblies from when cleavage of cyclic progelators is complete. TCEP reduction is shown to be reversible through TCEP inactivation at lower pH FIG. 23a, Progelator treated with 1.2, 2.4, and 3.6 eq of TCEP. Gradual decrease in pH (pH 7.4 to 4.5) occurs from successive TCEP additions. Neutralization to pH 7.4 with NaOH revives TCEP reductive potential.
Figure 24:
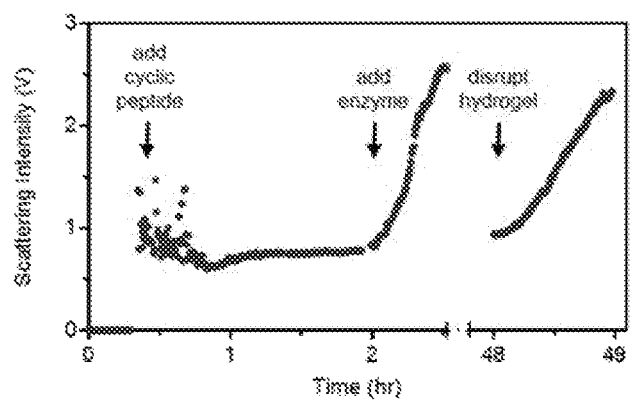
FIG. 24. SLS of cyclic progelator before and after enzyme addition. This scattering profile demonstrates that progelator in solution is stable to flocculation for hours until addition of thermolysin induces a steep increase in scattering intensity as self-assembly occurs. Complete disruption of macromolecular structures via sonication at 48 hr post-activation results in a return to nominal scattering intensity like that of the cyclic progelator. Reassembly is observed by a gradual increase in scattering intensity of this dilute solution. Final peptide concentration is 1 mg/mL in 1×DPBS at 37° C. Hydrogel disruption was achieved with 10 min sonication.

To understand the initial stages of self-assembly when progelators first encounter their target protease in vivo, slow step-wise cleavage of KFDF (SEQ ID NO:1)$_{Cyclic}$ progelator was achieved through serial additions of dilute thermolysin (FIG. 6f). CD reveals that linearization by enzyme cleavage causes an increase in peptide flexibility, shown by a steep decrease in the signal at 204 nm, and unchanged β-sheet signal from lateral alignment at 215 nm. Tris(2-carboxyethyl)phosphine (TCEP) was used as a positive control to represent ideal assemblies of linearized peptides through complete reduction of the disulfide bond (FIG. 6f and FIGS. 23a-23b). By TEM, reduced peptides assemble as tangled fibrils, similarly to enzymatically cleaved peptides (FIG. 6g). Thus, the enzyme-induced gels observed in FIGS. 6a-6g are likely forming through the same self-assembly mechanisms predicted with KFDF (SEQ ID NO:1)$_{Control}$. The rheological and spectroscopic results presented here indicate that our system has to potential to tolerate excess proteolytic degradation in vivo.

Figures 7A, 7B, 7C, 7D:
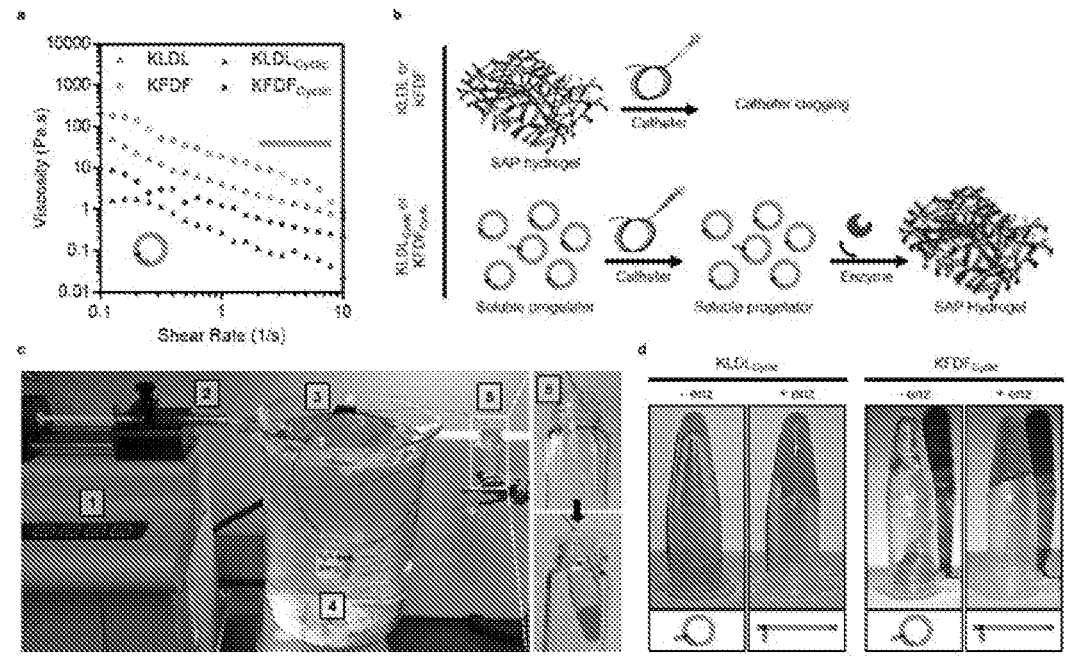
FIGS. 7a-7d. In vitro catheter injection of low viscosity progelators.

Catheter compatibility of cyclic peptide progelators. Minimally invasive injection of hydrogels into the heart is typically performed through transendocardial injections. Unlike direct epicardial injections performed in small animal models, transendocardial delivery has certain constraints that are not amenable to most hydrogel systems, namely materials should be able to reside within the catheter during an up to hour long procedure, yet still be injectable over multiple injections during this time, and finally only form a solid gel once it has entered the tissue.[17,51] Rapid gelation and/or high viscosity prohibit many injectable hydrogels from being considered for this minimally invasive delivery route. KLDL (SEQ ID NO:5)$_{Cyclic}$ and KFDF (SEQ ID NO:1)$_{Cyclic}$ progelators were amenable to cardiac catheter injection (FIGS. 7a-7d). As shown in FIG. 7a, both unmodified SAPs and cyclic progelators exhibit shear-thinning behavior, but the viscosities for the latter are over 20× lower for both KLDL (SEQ ID NO:5)$_{Cyclic}$ and KFDF (SEQ ID NO:1)$_{Cyclic}$. Thus, conformational constraint of β-sheet forming SAPs was sufficient to disrupt favorable unimer alignment and weakened structural interactions. We reasoned that SAP cyclization would be sufficient to prevent clogging during catheter injection (FIG. 7b).

To mimic injection of the cyclic progelators through a cardiac injection catheter in vivo, both (2 mol % labeled for visualization) were flowed through the inner nitinol tubing of a 27 G (0.21 mm inner diameter) MyoStar transendocardial injection catheter at 37° C. using a syringe pump (FIG. 7c). No excess resistance was detected by manual operation following incubation of cyclic progelator within the catheter loop for 60 min for either peptide. In contrast, unmodified KLDL (SEQ ID NO:5) and KFDF (SEQ ID NO:1) SAPs caused immediate catheter clogging. Excess resistance from high viscosity and tendency to rapidly self-assemble during shearing injection could explain why there are no previous reports of SAPs for cardiac catheter delivery. To ensure that the shear forces the cyclic progelator are exposed to during catheter injection do not inhibit enzyme activation and prevent gelation in vivo, the cyclic peptides were injected through the catheter into a vial containing thermolysin and incubated for 3 hr (37° C.), resulting in hydrogel formation (FIG. 7e).

Figures 8A, 8B, 8C, 8D, 8E, 8F, 8G:
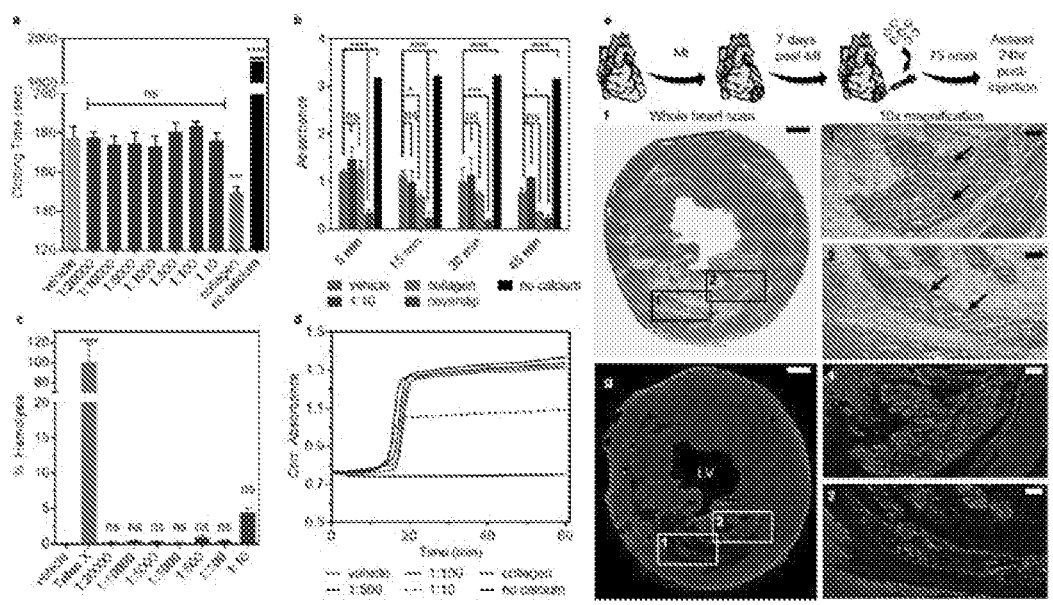
FIGS. 8a-8g. Hemocompatibility in human blood and in vivo analysis in a rat ischemia reperfusion model.
Figures 9A, 9B, 9C, 9D, 9E, 9F:
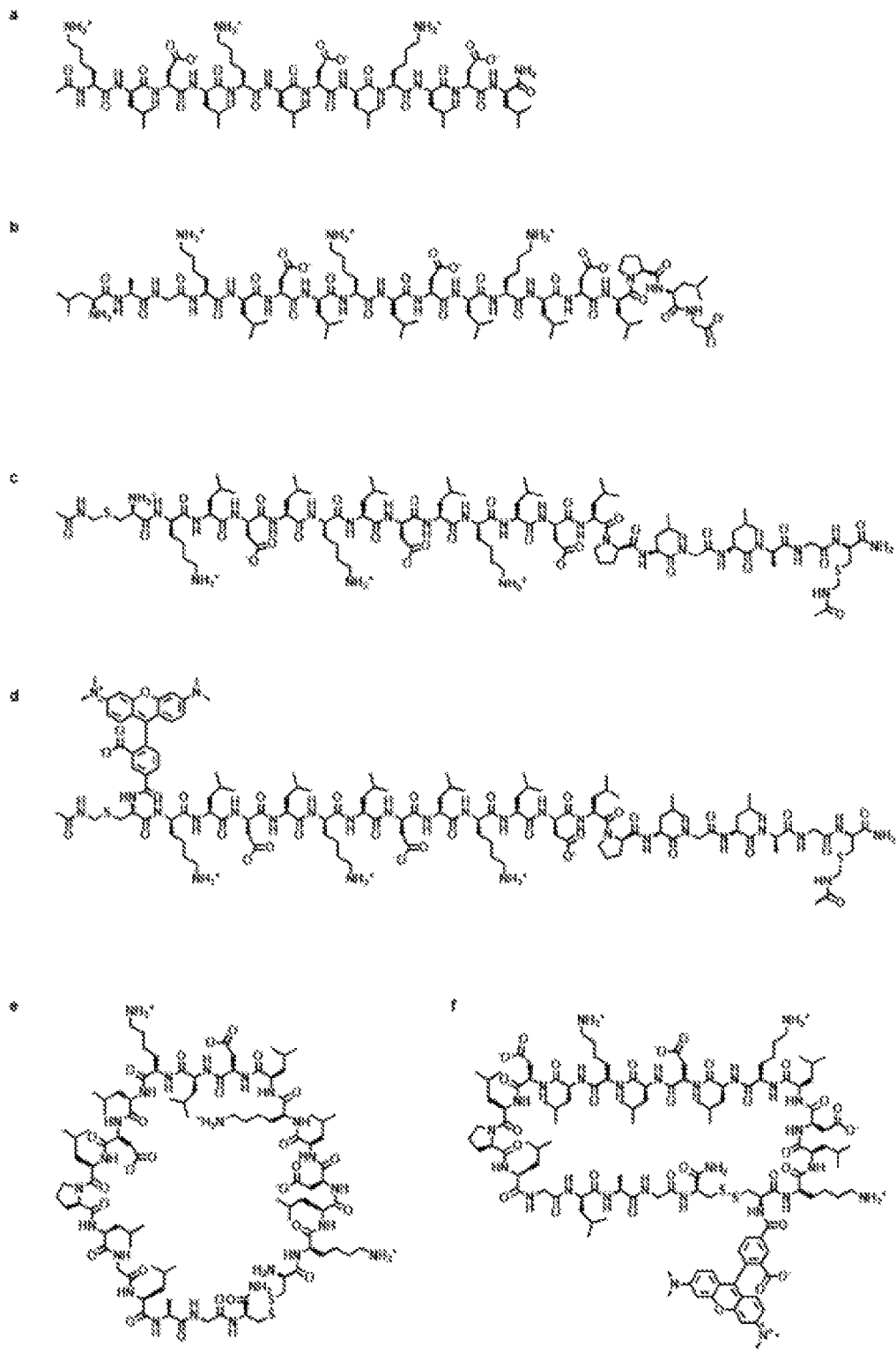
FIGS. 9a-9f. Chemical structures of KLDL (SEQ ID NO:5) peptides synthesized.
Figures 10A, 10B, 10C, 10D, 10E, 10F:
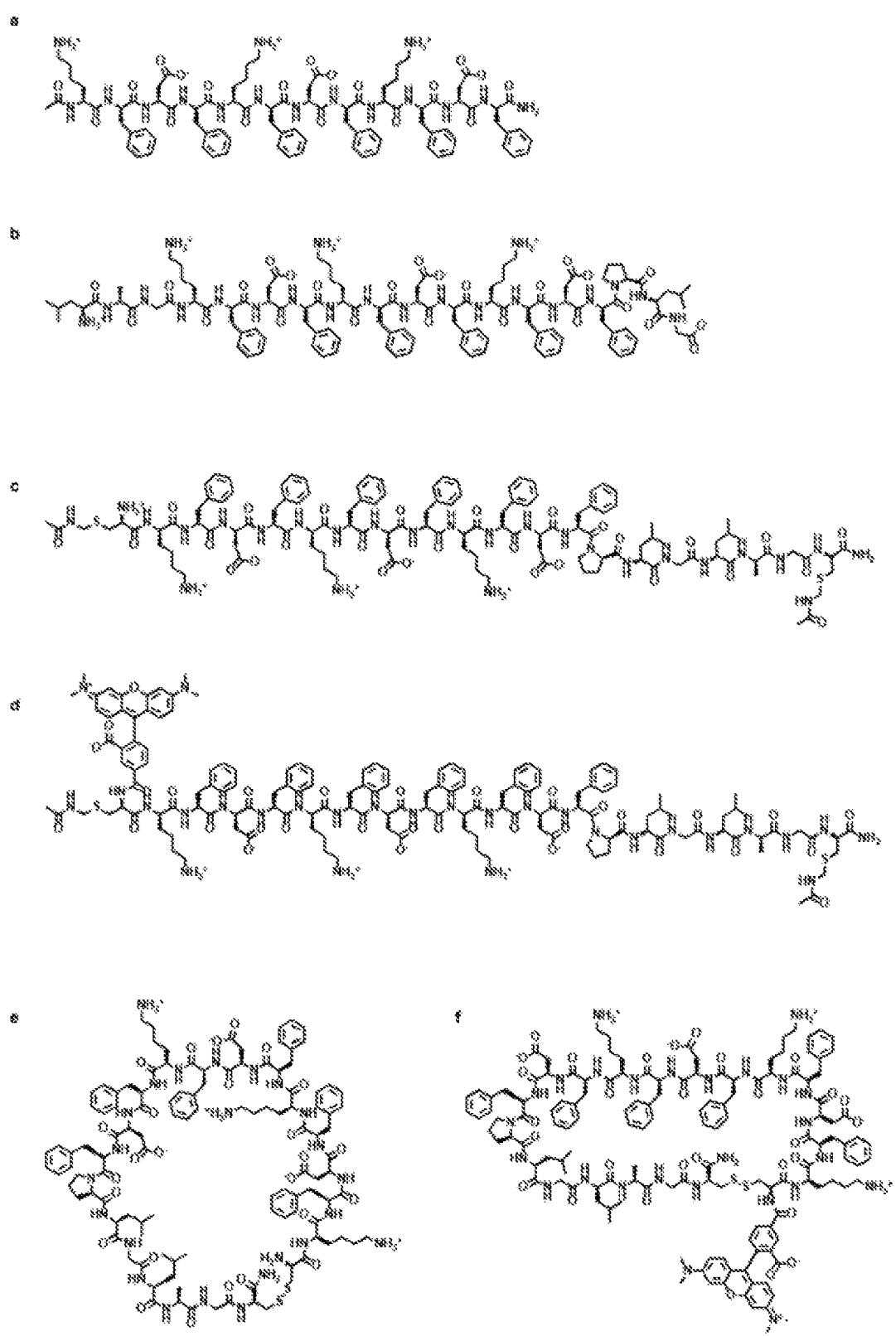
FIGS. 10a-10f. Chemical structures of KFDF (SEQ ID NO:1) peptides synthesized.
Figures 11A, 11B, 11C, 11D, 11E, 11F, 11G, 11H, 11I, 11J, 11K, 11L, 11M:
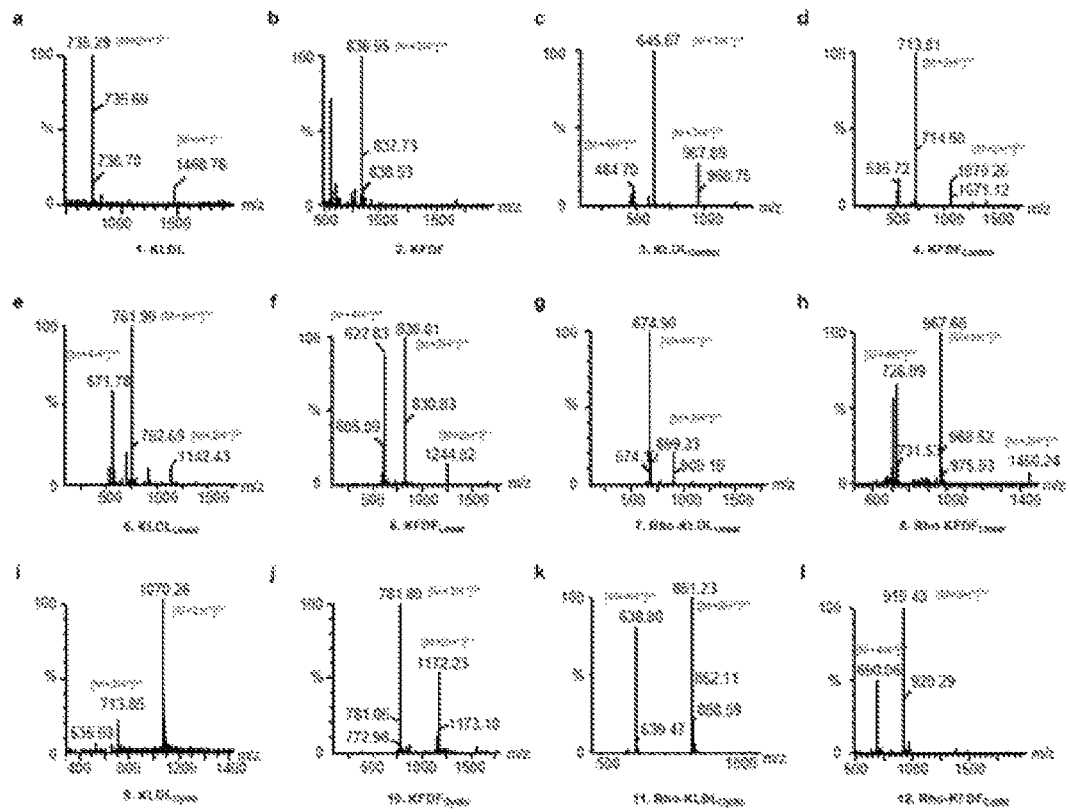
FIGS. 11a-11m. ESI mass spectra and sequences of peptides synthesized.
Figures 12A, 12B, 12C, 12D, 12E:
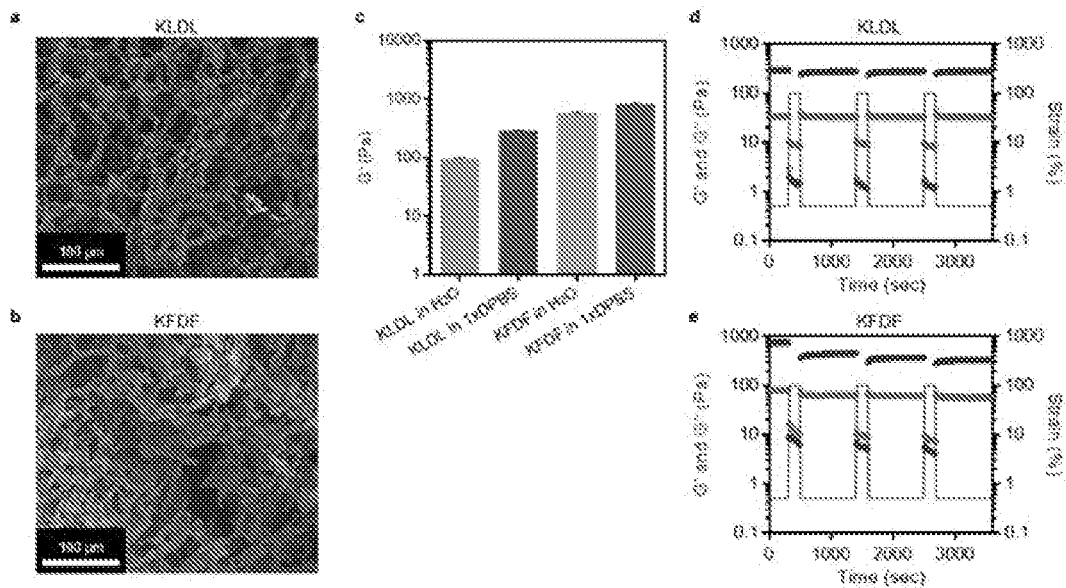
Figures 13A, 13B, 13C, 13D, 13E, 13F:
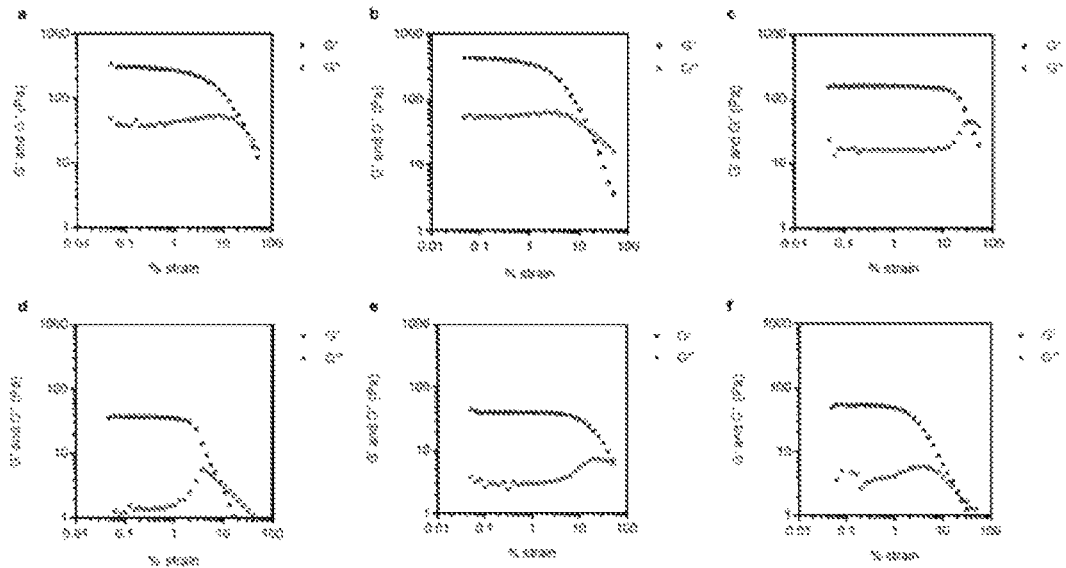
FIGS. 13a-13f. Strain sweeps of SAPs.
Figures 14A, 14B, 14C, 14D:
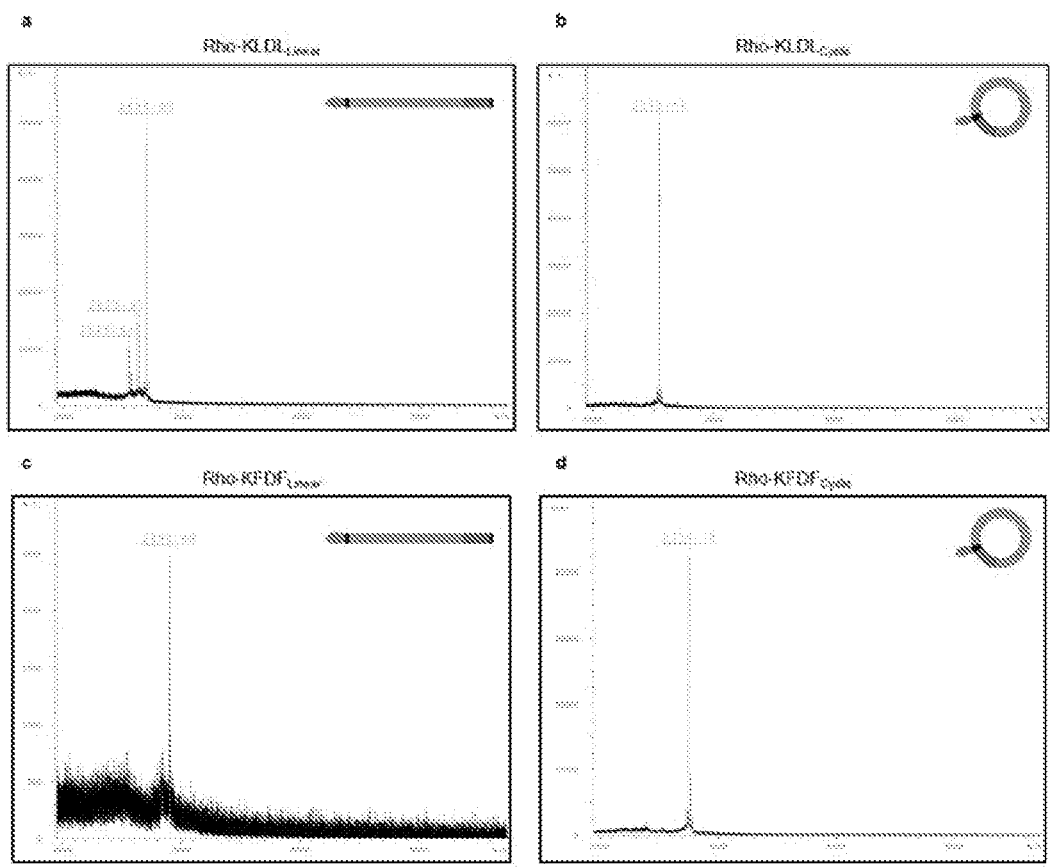
FIGS. 14a-14d. MALDI of labeled progelators before and after cyclization.
Figures 15A, 15B, 15C, 15D, 15E, 15F:
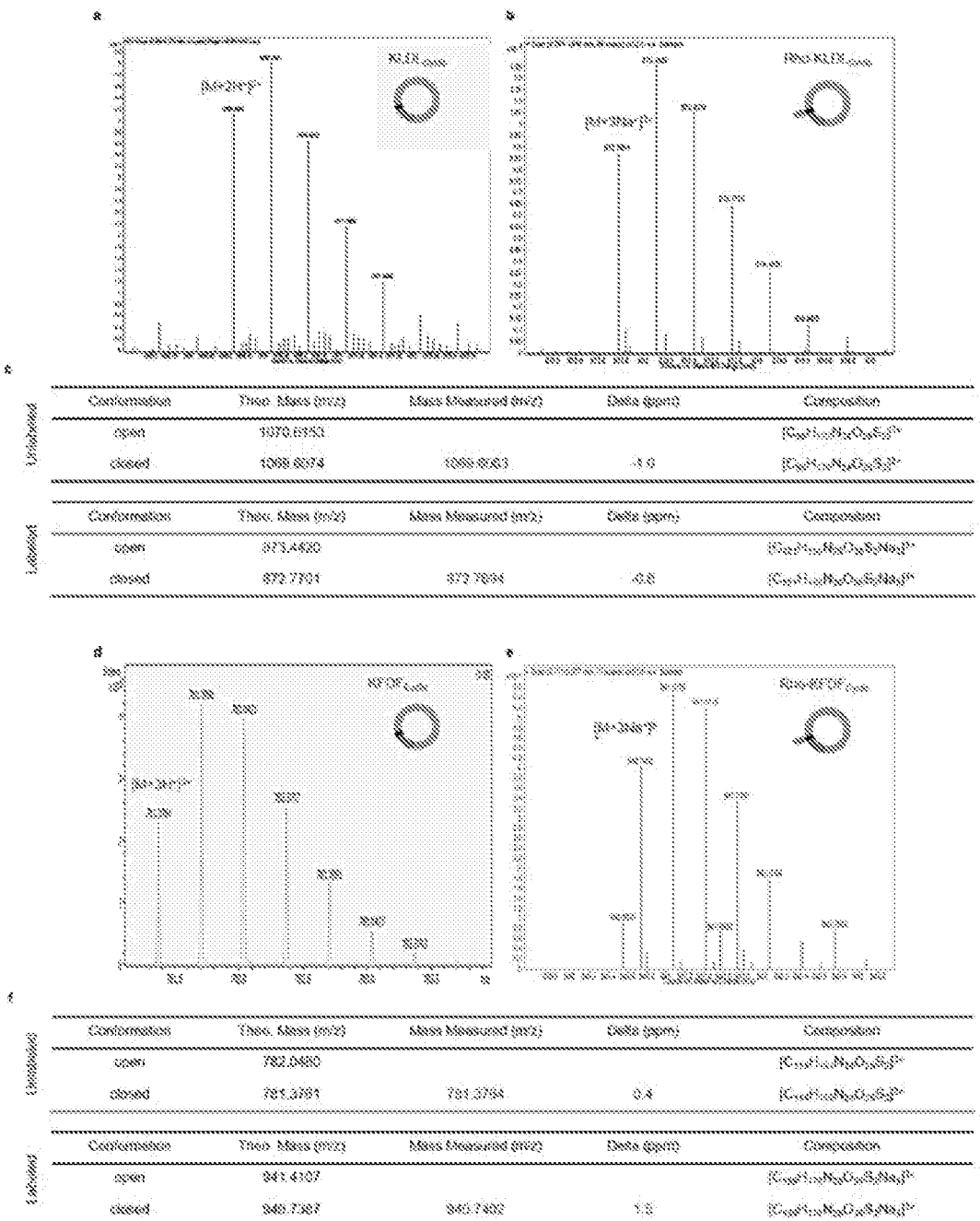
FIGS. 15a-15f. HRMS unlabeled and labeled progelators. Analysis conducted to identify whether final progelator peptides were in closed cyclic or open linear conformations.
Figures 16A, 16B, 16C, 16D:
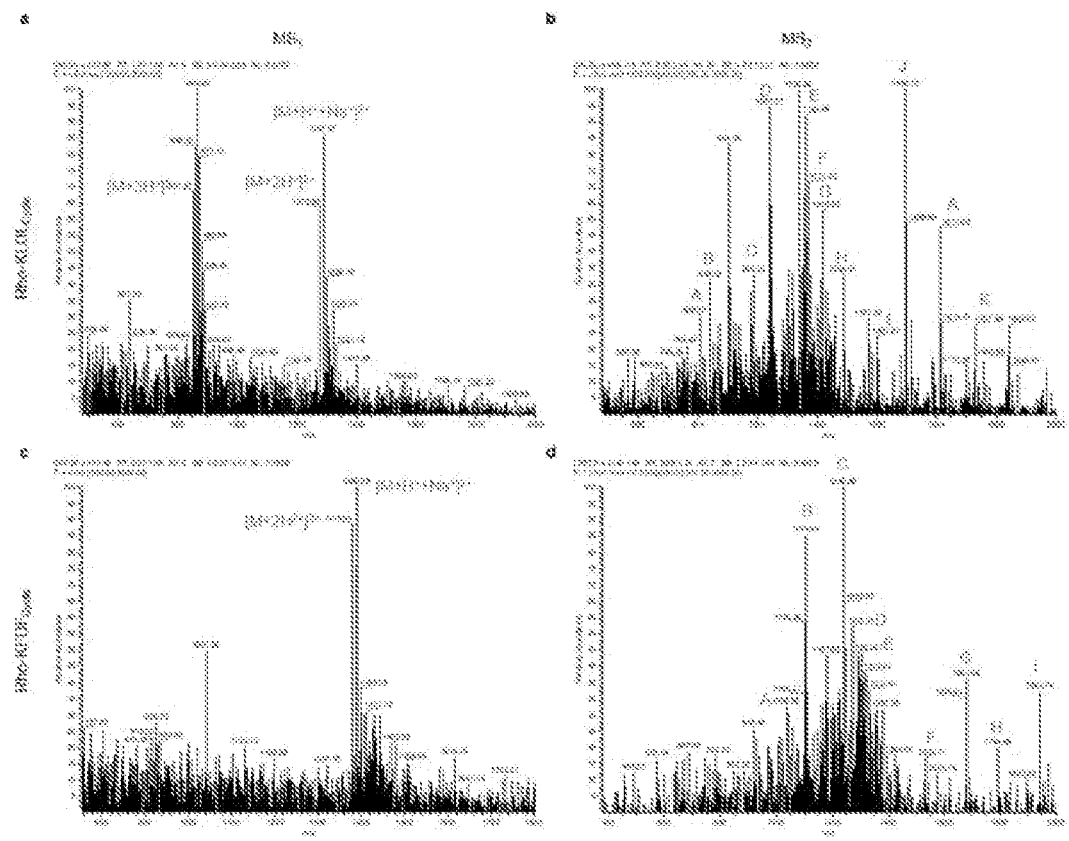
FIGS. 16a-16d. Tandem-MS of Rho-KLDL (SEQ ID NO:5)$_{Cyclic}$ and Rho-KFDF (SEQ ID NO:1)$_{Cyclic}$ progelators. Fragmentation of the peptide sequence enables identification of the peptide sequence, notably those that contain the less labile covalent disulfide bond.
Figure 25:
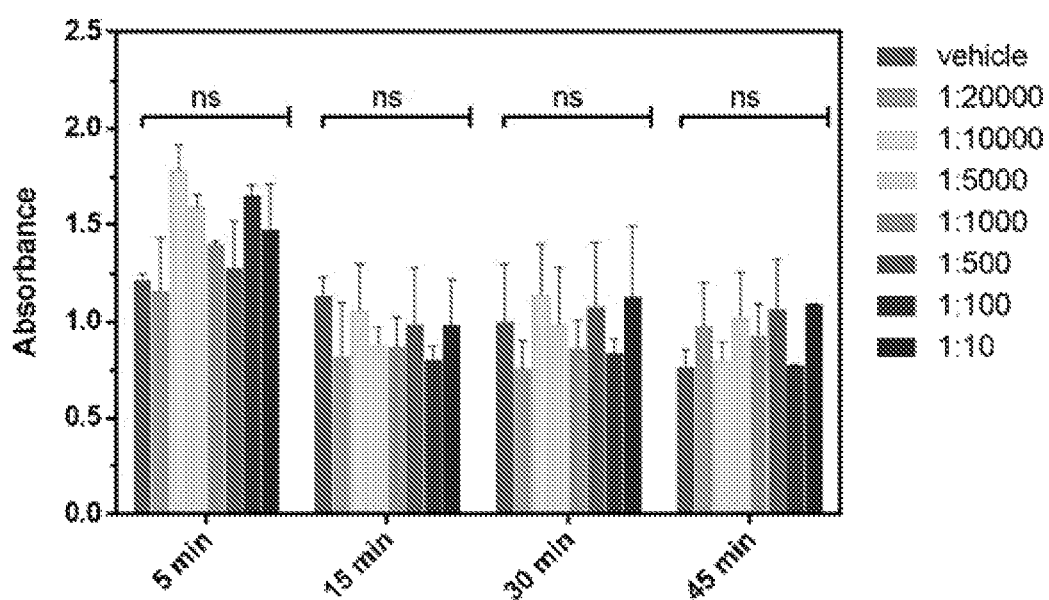
FIG. 25. Hemostasis kinetics as a response of dosing. Supplementary data corresponding to FIG. 8b in main text. Extent of clotting measured as absorbance at 405 nm as a function of dosing at 5, 15, 30, and 45 min in whole human blood. ns (p>0.05). (n=4 per group). Two-way ANOVA at each timepoint for comparison with vehicle standard. Values are mean±SEM.

Hemocompatibility and intramyocardial injections in a rat myocardial infarction model. For proof-of-concept analyses in biological systems, we examined the KFDF (SEQ ID NO:1)$_{Cyclic}$ progelator in hemocompatibility studies and assessed in vivo gelation (FIGS. 8a-8g). Biomaterial leakage is a concern with transendocardial injection since injections are performed into a beating heart.[52] Therefore, we assessed hemocompatibility of the cyclic progelator to ensure that modification and cyclization of the SAPs would not generate a thrombogenic response. Whole human blood clotting times, hemostasis kinetics, red blood cell (RBC) hemolysis, and pro-thrombotic profiles were evaluated in the presence of increasing cyclic peptide progelators concentrations in blood. Activated clotting times (ACT) were used as a standard method[53] that encompasses intrinsic and common coagulation pathways to assess thrombogenicity. Furthermore, as this method is influenced by increased sample viscosity due to clot formation, potential peptide cleavage by blood proteases and resulting self-assembly would decrease clotting times. No adverse effects were observed for up to 1:10 peptide:blood concentrations (FIG. 8a and Table 5). In contrast, collagen showed a significant clot time reduction, and chelation of calcium prevented clotting altogether. Whole blood clotting kinetics were also measured in the absence of an activator to monitor the influence of progelator on hemostasis. Similarly, no statistical difference in clotting was observed between the vehicle and the highest progelator concentration (1:10) at any timepoint (FIG. 8b and FIG. 25). In contrast, collagen and glass controls increased the clot rate.

Figures 26A, 26B, 26C:
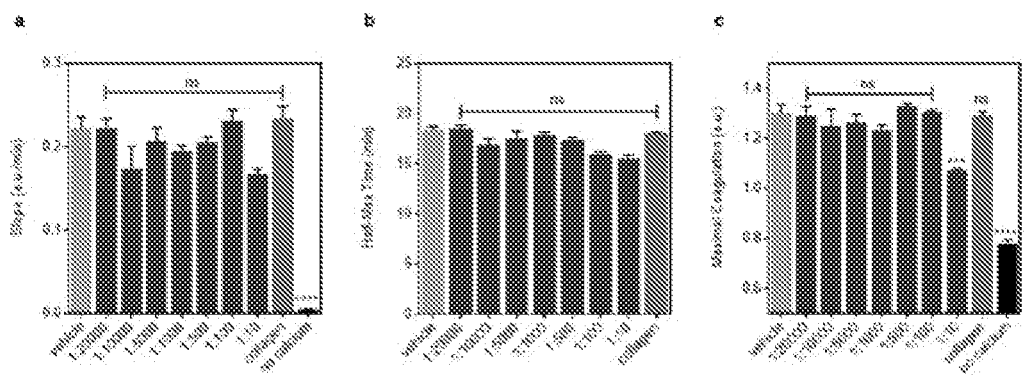

Red blood cell (RBC) hemolysis in the presence of progelator was used to assess acute toxicity (FIG. 8c and Table 6). Doses up to 1:10 revealed <5% hemolysis, which is below the limit for consideration as a nonhemolytic biomaterial.[54] Finally, a pro-thrombotic assay using platelet poor plasma (PPP) was used to monitor non-platelet and phospholipid-specific effects on blood (FIG. 8d), such as potential to inhibit thrombin activity, prevent crosslinking of fibrinogen, or sequestration of calcium for decreased platelet activation. This assay has the advantage of monitoring the intrinsic pathway only, which is useful for studying surface contact activation in blood-biomaterial interactions. The onset of coagulation is indicated by a steep rise in the absorbance vs time curve. A plateau in absorbance was reached within a few minutes and maintained over time, indicating a fully formed, stable clot. No changes to coagulation rate (slope), half-maximal coagulation time, and extent of coagulation (FIGS. 26a-26c) were observed in samples incubated with progelator up to doses of 1:100 peptide/blood.

Figures 27A, 27B:
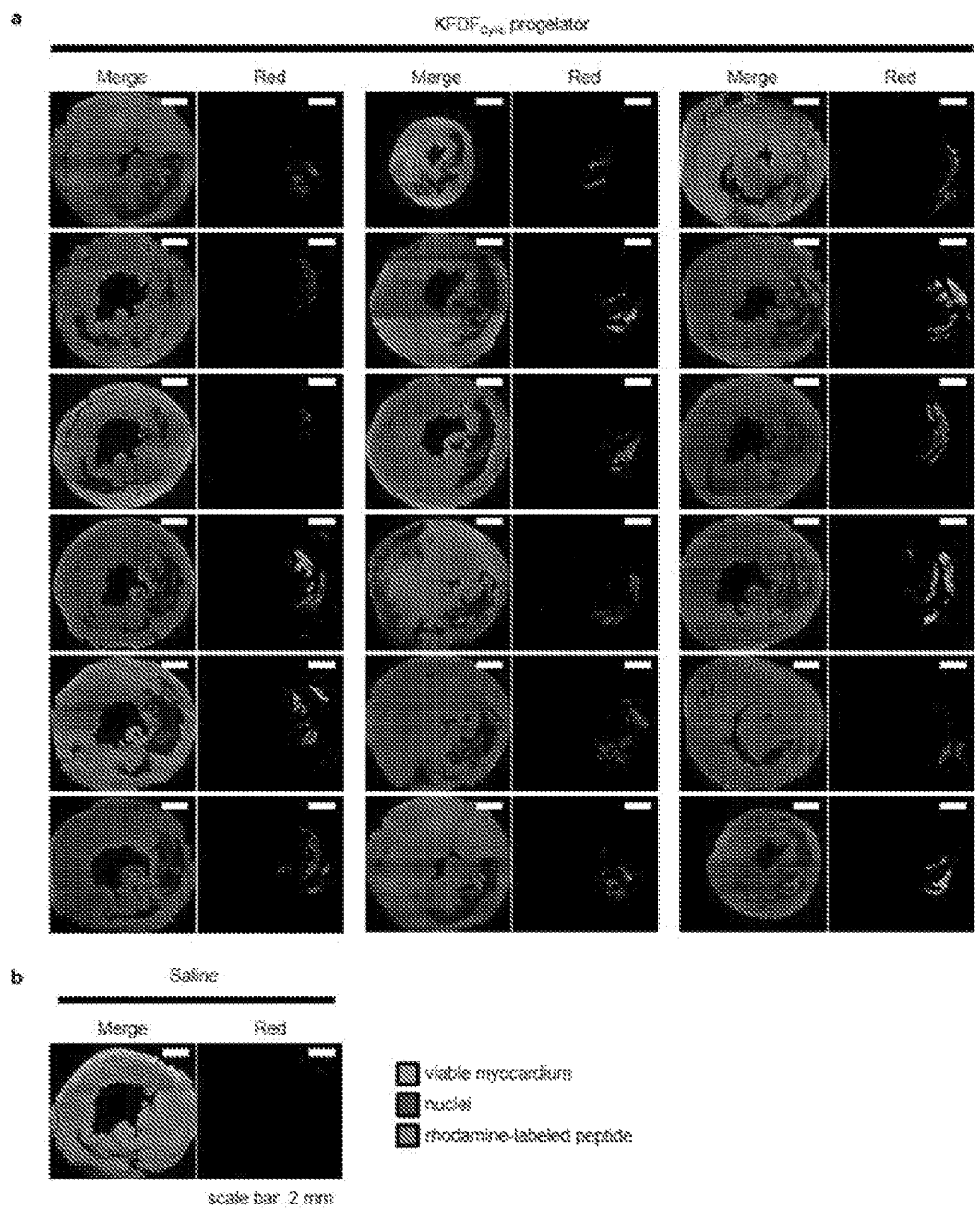
FIGS. 27a-27b. Heart slices visualized through IHC staining.

With hemocompatibility verified, we applied the progelator in an initial proof-of-concept study in vivo. Enzyme-responsive progelator, KFDF (SEQ ID NO:1)$_{Cyclic}$, doped with a small amount of Rho-KFDF (SEQ ID NO:1)$_{Cyclic}$ (5 mol %) for imaging, was injected into the infarct region 7 days post-MI in a rat ischemia-reperfusion model (FIG. 8e). Assessment of hearts at 24 hr post-injection confirmed that progelator effectively gelled at the heart (FIG. 8e, FIGS. 27a-27b). Histological and fluorescence analysis of heart sections revealed hydrogel assembly occurred at the site of MI in all rats (FIGS. 8f-8g). This experiment demonstrates the activation and subsequent gelation of MMP responsive progelators to inflamed biological tissue.

The number of candidate biomaterials amenable to minimally invasive cardiac catheter delivery to the heart post-MI is limited. Consequently, translation of promising scaffolds from preclinical to clinical trials has been rare. Provided herein is a platform modification strategy to enable one class of hydrogels, SAPs, to be injectable via a cardiac injection catheter by conformationally constraining linear SAPs into macrocyclic progelators which resist self-assembly (FIGS. 1a-1c). These progelators were further modified with a substrate recognition sequence for endogenously expressed MI-associated proteases. The invention provides peptide sequences based on a known SAP, and then utilizing in silico modeling to provide preliminary insight into any modifications that may cause disruption of gelation (FIGS. 2a-2c). These modified sequences were then prepared synthetically for testing. Subsequent experimental analysis of self-assembly characteristics and mechanical properties agreed well with these predictions, namely that sequences modifications did not interfere with self-assembly as β-sheets into fibrils and viscoelastic hydrogels (FIGS. 3a-3h). It is hypothesized that the platform for modifications could be well-tolerated by other known SAP sequences used for biomedical applications.[55,56]

The versatility of the platform is demonstrated through the functionalization of two different SAPs sequences, which exhibit disparate self-assembly mechanisms, and yet form progelators with identical responsiveness. Cyclic progelators synthesized in FIGS. 4a-4k lacked the capacity to gel when sterically constrained. However, they exhibited responsiveness to enzymes that are inherently active in the MI during both the acute inflammatory phase and fibrotic phase (FIGS. 5a-5f). Despite the different cut sites recognized by MMP-9 catalytic domain, elastase, and thermolysin, similar secondary structure and nanoscale morphology changes were observed. Bulk cleavage of these sterically constrained materials resulted in healable viscoelastic hydrogels that were stable against excess proteolysis (FIGS. 6a-6g).

The development of smart structurally dynamic and responsive materials for tissue engineering post-MI is a relatively untapped field. With many scaffolds, the common issue remains that chemical modification (e.g. crosslinks, binding moieties, targeting motifs, or therapeutics drugs) can negatively impact material properties such as sample viscosity and gelation kinetics, which would preclude their use in catheters. With the present design, mechanical differences (e.g. stiffness or healing kinetics) in the resulting hydrogel would not affect the initial progelator formulation.

Importantly, we provide the first demonstration of low viscosity peptide-based progelators for use in a cardiac injection catheter with little resistance to flow (FIGS. 7a-7d). The results of these experiments demonstrate that the cyclic progelator acts as a Newtonian fluid for smooth catheter-based injection and still retains the capacity to solidify when acted upon by endogenously expressed inflammatory enzymes in the heart, suggesting this could provide a useful strategy for cardiac catheter delivery in vivo.

With the potential for tissue leakage into the bloodstream, thrombogenicity of transendocardially injected biomaterials is a concern. Synthetic modifications to the KFDF (SEQ ID NO:1) SAP were shown to be hemocompatible and non-thrombogenic through a comprehensive assessment of whole blood clotting times, hemostatic kinetics, RBC hemolysis, and pro-thrombotic assays (FIGS. 8a-8g). A dosing analysis shows no statistically significant difference in hemostasis due to increasing progelator concentration in whole blood. The extent of coagulation in platelet poor plasma was only altered at the highest peptide dose which indicates that local high concentrations of peptide have an minor anti-coagulative effect on the intrinsic coagulation (contact-based) pathway; furthermore, the impact that the peptide does have on coagulation was shown to be independent of platelet-dependent thrombus formation, a key player in the pathogenesis of acute MI.[57] This conclusion is supported by the lack of change in pro-thrombotic profiles when incubated with collagen, which increases clotting rates only through the activation of platelet aggregation.[58] Given a "standard" clinical concentration of 1:10,000,[59] which assumes that no material was injected into the heart wall and instead escaped into the bloodstream, no adverse effects were observed on coagulation at this clinically relevant dose. These results indicate that this platform for generating an inert cyclic adduct of known SAPs should not result in unwanted blood interactions during delivery.

The present platform enables facile delivery of a free-flowing progelator, and on-demand gelation at the site of inflammation (FIG. 8). In vivo analysis of KFDF (SEQ ID NO:1)$_{Cyclic}$ progelator revealed successful gelation of activated hydrogel scaffolds in a rat MI model. As such, the invention demonstrated a simplistic strategy that uses the naturally complex MI microenvironment for delivery and smart assembly in tissue. This proof-of-concept test paves the way for exploring the amenability of various other SAP systems (e.g. RAD16-II) with the progelator system for cardiac catheterization in vivo. In addition, there exists the potential to combine this approach with various therapeutics. In this study, appendage of a rhodamine dye to cyclic progelators did not disrupt gelation. The invention envisions a modular system to deliver and sustain any number of covalently bound therapeutics (e.g. small molecule drugs or short peptides). For larger therapeutics (e.g. stem cells and growth factors), simple formulation as a nonviscous solution for delivery, and subsequent encapsulation within the locally activated networks, might provide a means for targeted drug delivery without the need for complex synthetic manipulation. Ultimately, the simple strategy for structural control of self-assembling peptides can be employed for minimally invasive delivery of therapeutic peptides to other forms of injury or disease where MMPs are upregulated, including osteoarthritis,[60] cartilage tissue repair,[41] nerve damage[61,62] and acute brain injury[63].

General information. Amino acids used in Fmoc SPPS were purchased from AAPPTec and NovaBiochem. All other synthetic materials were obtained from Sigma-Aldrich and used without further purification unless otherwise noted. MMP-9 (recombinant human catalytic domain) (BML-SEro360) was acquired from Enzo Life Sciences, as a 1.0 mg/mL solution at 40 U/μL in 50 mM TRIS, pH 7.5, 1 mM $CaCl_2$, 300 mM NaCl, 5 μM $ZnCl_2$, 0.1% Brij-35, and 15% glycerol. Porcine pancreatic elastase (3246821000U) was acquired from EMD Millipore, as a lyophilized powder (22 U/mg). Thermolysin (V400A) was acquired from Promega, as a lyophilized powder. Unspun whole human blood (citrated, non-heparinized) was obtained from Biological Specialty Corporation (LS23 95099) and stored at 1-6° C.

Peptide synthesis. Peptides were synthesized in an AAPPTec Focus XC peptide synthesizer. Peptides with C terminal amides were synthesized on rink amide MBHA resin and peptides with C-terminal carboxylic acids were synthesized on Wang-OH resin using double coupling conditions for the first amino acid. HBTU (N,N,N',N'-tetramethyl-O-(1H-benzotriazol-1-yl) uronium hexafluorophosphate) was used as the general coupling agent. When included, rhodamine was incorporated during the synthesis at the N-terminus of the sequence as 5(6)-carboxytetramethyl rhodamine using HATU (1-[Bis(dimethylamino)methylene]-1H-1,2,3-triazolo[4,5-b]pyridinium 3-oxid hexafluorophosphate) as the coupling agent. 5(6)-carboxytetramethyl rhodamine was synthesized as previously described.[64] General peptide cleavage and deprotection was performed in 95:2.5:2.5 (% v/v) trifluoroacetic acid (TFA), triisopropyl silane (TIPS), and $H_2O$, respectively, for 2 hr. Cleaved peptides were precipitated in cold anhydrous ether (3×) to yield solid crude. Semi-protected peptides containing Cys (acm) were purified prior to cyclization. To synthesize cyclic progelators, iodine was used to simultaneously deprotect Cys(acm) and initiate disulfide bond formation under dilute conditions to favor intramolecular macrocyclization.[65] To a solution of semi-protected peptides (500 μM) in a mixture of acetic acid/methanol/$H_2O$ (1:16:4) was slowly added 0.1 M methanolic iodide until the yellow color persisted (~4-5 eq). The reaction was vigorously stirred at room temperature for 2 h and reaction completion was confirmed by LCMS. After 2 hr reaction, Amberlite IRA-400 Resin (chloride form) was stirred in the solution for 1 hr to quench excess iodine and absorb reacted iodide ions. Filtrated was placed on a rotary evaporator to remove acetic acid and methanol. The remaining solution was diluted with $H_2O$ and lyophilized to a white powder. By HPLC no dimerization was observed. For cyclization kinetics analysis (FIGS. 2c-2e), the N-terminal Fmoc was temporarily left on unlabeled peptides for improved peak separation during purification.

Peptide purification and analysis. Analytical scale RP-HPLC analysis of peptides was performed on a Jupiter Proteo90A Phenomenex column (150×4.60 mm) using a Hitachi-Elite LaChrom L2130 pump with a UV-Vis detector (Hitachi-Elite LaChrom L-2420) monitoring at 214 nm, 256 nm, 290 nm, and 565 nm. Gradients performed over 30 min. LCMS was performed with a Waters AQUITY UPLC System using a C-18 column over a 4 or 10 min gradient. Peptides were purified with a Jupiter Proteo90A Phenomenex column (2050×25.0 mm) on an Armen Glider CPC preparatory phase HPLC over a 43 min gradient to yield 90-95% purity. For all RP-HPLC assays and purifications, gradient solvent systems utilized Buffer A ($H_2O$ with 0.1% TFA) and Buffer B (acetonitrile with 0.1% TFA). For all LCMS assays, gradient solvent systems used Buffer A ($H_2O$) and Buffer B (acetonitrile with 0.1% formic acid). Crude peptide was prepared for purification in 5:25:70 acetic acid/Buffer A/Buffer B via initial dissolution in acetic acid with sonication, followed by addition of ACN then $H_2O$. Unless otherwise stated, peptides were purified using a gradient of 25-45% Buffer B over 30 min and 50 min for analytical HPLC and preparatory phase HPLC, respectively. Following purification, product was analyzed by ESI to verify identity (see FIGS. 11a-11m). Due to the large number of cis/trans configurational isomers that our cyclic progelators could adopt,[66,67] and amphiphilic self-assembling nature of our peptides, peak resolution via HPLC was low in many instances. We relied on various mass spectrometry techniques (ESI, MALDI, HRMS, and Tandem-MS) to verify purity of isolated materials.

Mass spectrometric (MS) analysis of peptides. General mass spectra were obtained at the UCSD Chemistry and Biochemistry Molecular Mass Spectrometry Facility using a Micromass Quattro Ultima Triple Quadrupole Electrospray Ionization (ESI) mass spectrometer or Bruker Biflex IV MALDI-TOFMS using HCCA (1:1 v/v) as the matrix. HRMS on a Thermo LTQ Orbitrap XL IS and Tandem-MS on a Thermo LCQdeca-MS were collected for cyclic progelators to discern conformation as cyclic or linear. DisConnect software[68] was used to unambiguously characterize disulfide connectivity. The following settings were used: $MS^2$ fragmentation ions, monoisotopic mass calculations, tolerance ±3 Da, normal peptide fragments (no losses), and calculations based on ion-trap filtering.

UV Absorbance Spectra. UV absorbance spectra of peptide labeling was measured on a ThermoScientific Nanodrop 2000c.

Progelator sterilization and formulation for in vivo analysis HPLC purified peptides were dialyzed with 1 kDa MW cutoff tubing into milliQ $H_2O$, sterile filtered through a 0.2 μm PES filter, and lyophilized to a powder. Peptide was reconstituted prior to injection with sterile pH 9 $H_2O$ to form a clear solution (11.11 mM) then diluted further with sterile 10×DPBS to a final concentration of 10 mM peptide in 1×DPBS (pH 7.4). Solutions for in vivo analysis contained 5 mol % rhodamine labeled progelator (0.5 mM labeled+9.5 mM unlabeled) for fluorescence imaging purposes.

Transmission electron microscopy (TEM). Formvar/Carbon-coated 400 mesh Cu grids (Ted Paella, Inc.) were glow discharged for 90 s and spotted with 4-5 μL peptide sample (100 μM) and set for 5 min. Grids were washed with distilled $H_2O$ (10 drops), stained with 1% w/w uranyl acetate (3 drops), and wicked dry with filter paper. TEM images were acquired on an FEI Tecnai G2 Sphera at 200 kV.

Static and dynamic light scattering (SLS and DLS). Light scattering measurements were performed on a Wyatt DynaPro NanoStar at 37° C. (λ=657 nm). For each DLS measurement, 10 acquisitions for 10 sec were taken. Samples were prepared at 1 mg/mL in either $H_2O$, 1×DPBS, or 295 mM sucrose (pH 7.4). Experiments with enzyme activation used 1:4500 enzyme/substrate molar ratio. Experimental circular dichroism (CD). Peptides were dissolved at a final concentration of 125 μM (labeled peptides) or 500 μM (unlabeled peptides) in 10 mM Tris buffer or $H_2O$ (for TCEP reduction only) at pH 7.4, to reduce signal interference seen with DPBS at lower wavelengths. UV-Vis circular dichroism (CD) was measured on a Jasco J-810 Spectropolarimeter to evaluate the secondary structure of peptide samples. Measurements were taken using the following settings: wavelength range=190-260 nm, scanning speed=50 nm/min, response time=2 s, data pitch=1 nm, band width=1 nm, accumulations=3, pathlength=1 mm, and temperature=37° C. Spectra are presented as an average of all accumulations. Sample voltage was monitored to verify the signal intensity did not exceed 800 mV within the wavelength range. Spectra were converted from units of millidegrees (mdeg) to molar ellipticity [θ] using the following equation:

$$[\theta] = \frac{mdeg * M}{C * L * 10},$$

where mdeg is the measured absorbance of circularly polarized light, C is concentration in g/L, M is the mean residual weight in g/mol, and L is the cell pathlength in cm.

Computational modeling with FibPredictor. FibPredictor was utilized as a commercially available software for generating native-like amyloid fibril structures.[42] This software was chosen for our study due to its unique ability to reliably model all classes of amyloid fibrils starting from sequence-only input. The algorithm combines β-sheet model building, -sheet replication, and symmetry operations with side-chain prediction and statistical scoring functions, for computational predictions on amyloid fibril structures of self-assembling peptides utilized in this study. From each random model generated, a SCRWL internal scoring function was used by SCWRL4 to predict the energetically lowest side chain orientations. This scoring function was used to calculate the minimal total energy of the entire model and outputs coordinates for the structure as a PDB file with predicted side chains using the same residue numbering and chain identifiers as the input structure. To identify the most energetically favorable candidate structures in the ensemble, both Amb_3b (computationally more efficient)[69] and GOAP (more accurate)[70] statistical scoring functions were used to calculate total energies of the protein structure. Reported energies are unitless as they are empirically derived scores, thus it is not advisable to interpret results as kcal/mol. Normalized GOPA scores are useful for comparing fibrils of different sizes. Three generations of modeling were performed with literature-recommended parameters shown in Table 1. Results of top model for each peptide sequence from the third-generation analysis are reported in Table 2. Corresponding structures and raw PDB files are provided in the main text FIG. 2. Output PDB files, containing the atomic coordinates of the chromophores, from top models were used to generate theoretical CD spectra with Dichro-Calc.[45]

Theoretical CD spectra with DichroCalc. DichroCalc was used to calculate CD spectra using predicted PDB from FibPredictor. This web interface predicts secondary structure type using a variety of matrix method parameters, which have been derived from ab initio calculations.[45] These parameters include the peptide chromophore in the far-UV, charge-transfer between neighboring peptide groups in the deep-UV, and aromatic side chain chromophores with transitions in the near-UV. Full analysis CD spectra were output in units of molar ellipticity [θ] vs wavelength.

In vitro enzyme cleavage of cyclic peptide progelator. Unless otherwise stated, enzyme cleavage experiments were performed on progelator at a final concentration of 500 μM in 1× enzyme cleavage buffers. MMP-9 cleavages were performed at 1:1000 enzyme/substrate molar ratio in 1× buffer (50 mM Tris-HCl, 200 mM NaCl, 5 mM $CaCl_2$, 1 mM $ZnCl_2$, pH 7.5) for 5 hr. Elastase cleavages were performed at 1:250 enzyme/substrate molar ratio in 1× buffer (100 mM Tris-HCl, 0.2 mM $NaN_3$, pH 8.0), and thermolysin (50 mM Tris-HCl, 0.5 mM $CaCl_2$)) for 5 hr. Thermolysin cleavages were performed at 1:4500 enzyme/substrate molar ratio in 1× buffer (1×DPBS, pH 7.4) for 15 min. Analysis of unlabeled cyclic peptide progelator cleavage by CD (FIG. 4c) was conducted with serials additions of thermolysin (4×1:18,000 enzyme/substrate) over a period of 73 hr. Control samples utilized denatured enzymes under the same conditions. MMP and elastase were heat denatured with 10 min incubation at 65° C. Thermolysin was inactivated by incubation with 10% (v/v) EDTA (0.5 M, pH 8.0)

Rheological characterization. All peptide samples were prepared at 10 mM peptide, except for those used to assess the effect of SAP functionalization with respect to weight (15 mg/mL). Viscous and viscoelastic properties were assessed using a stress-controlled rheometer (TA Instruments AR-02) equipped with a Peltier plate to control temperature and a 20 mm diameter parallel plate geometry. Unless otherwise stated all measurements were taken at an angular frequency of 2.5 rad $s^{-1}$, strain of 0.5%, and temperature of 37° C. Measurements were performed with a gap height of 1000 μm and repeated three times (except for step-strain tests) to ensure reproducibility. To prevent water evaporation, mineral oil was wrapped around the edge of the geometry at the air-sample interface. For viscoelastic measurements the apparatus was used in oscillatory mode. To ensure the measurements were made in the linear viscoelastic regime (LVR), strain sweeps were performed between 0.05-50% strain and showed no variation in storage (G') and loss (G") moduli up to a strain of 0.5%. The dynamic moduli of the hydrogels were measured as a function of frequency in the range 0_25-100 rad $s^{-1}$ at a strain of 0.5%. Continuous step-strain oscillations were used to monitor hydrogel healing through disruption (3 min, 100% strain) and recovery (15 min. 0.5% strain) cycles (n=3). Temperature sweeps were measured by increasing the apparatus temperatures from 21-40° C. at a ramp rate of 0.5° C./min. For viscosity measurements the apparatus was used in steady state flow mode. The viscosity of the samples was measured as a function of shear rate in the range 0.1-10 $s^{-1}$ (5% tolerance.

In vitro catheter injections and effect on assembly. In vitro injection of peptide systems through the 27 G inner nitinol tubing of a MyoStar catheter was performed, as previously described.[51] Peptide solution (0.6-0.8 mL) was prepared at 10 mM in 1×DPBS (pH 7.4) and loaded into a 1 mL Leur Lock syringe attached to a syringe pump set to a flow rate of 0.6 mL/min. Catheters were inspected for potential clogging during injection.

Hemocompatibility analysis. For all measurements, peptide stocks in 1×DPBS were prepared such that the final concentration (v/v) in blood or plasma were 1:10, 1:100, 1:500, 1:1000, 1:5000, 1:10000, and 1:20000 (peptide:fluid volume). Controls with collagen as a procoagulant initial platelet-adhesive surface (0.095 mg/mL as per literature[71] or 1:240 dilution) or with calcium chelated by sodium citrate utilized 1×DPBS as a vehicle to ensure consistent blood dilution in all experiments. Peptide stocks, whole human blood, isolated red blood cells (RBCs), and platelet poor plasma (PPP) were warmed to 37° C. immediately prior to use. Plate reader measurements were conducted on an EnSpire Multimode Plate Reader with 96-well tissue culture plates (TCP).

Activated clotting times (ACT) with whole human blood. A Hemochron 801 instrument calibrated with an electronic system verification (ESV) device was used to measure activated clotting time (ACT) of whole human blood. Activated clotting times (ACT) were determined using recalcified citrated whole human blood to minimize variability in starting time points for clotting in all assays.[71] To each Hemochron P214 tube with glass beads was added 4 μL $CaCl_2$ (1.1 M) and 36 μL peptide stock or additive (12.2× final blood concentration). Samples were mixed thoroughly for 30 s to soak the glass beads and incubated 30 s at 37° C. Citrated whole human blood (400 μL) was then added (t=0 s), mixed by hand for 10 s, and added to the instrument. Time points at which the magnet was displaced by clot formation were recorded by the instrument. Collagen (0.095 mg/mL) was used as a positive control to increase clotting time. Vehicle (1×DPBS) served as a standard for blood without additive. Samples without calcium, serving as the negative control, exceeded instrument maximum time range (>1500 sec). Each experiment was performed n=6 times with averages and standard error of the mean (SEM) plotted.

Whole blood hemostasis kinetics. Changes to time-dependent hemostasis were monitored using a non-activated whole blood clotting assay.[72] Briefly, 100 μL of citrated whole human was mixed with 10 μL of peptide or collagen stock (11.5× final blood concentration) and 5 μL of $CaCl_2$ (230 mM). Collagen (0.095 mg/mL) and glass coverslips were used as positive controls to increase clotting rates from an additive and contact initiated perspective, respectively. Samples without calcium, where no clot was observed at any timepoint, served as negative controls. Aliquots (100 μL) were transferred to a 12-well TCP, covered, and incubated at r.t. for 5 min, 15 min, 30 min, and 45 min. Each sample was prepared in triplicate. At the end of each time point, RBCs not caught in the thrombus were lysed by gently adding 3 mL distilled $H_2O$ and incubating for 5 min. Each well was sampled (200 μL), taking care not to disturb the clot, and transferred to a 96 well plate for analysis. Released hemoglobin from lysis was detected by measuring the absorbance at 405 nm (height 4.0 mm, 100 flashes) using a plate reader. Extent of clotting is inversely proportional to measured absorbance. Averages (n=3) and standard error of the mean (SEM) are plotted.

Hemolysis assay. Acute toxicity of cyclic peptide progelator was measured with a RBC hemolysis assay specific to biomacromolecular drug analysis, as previously described.[73] Averages (n=4) and standard error of the mean (SEM) for absorbance measurements (at 540 nm) were plotted.

Pro-thrombotic assays. The intrinsic coagulation pathway was assessed using a pro-thrombotic assay, as previously described.[72] Collagen (0.095 mg/mL), which interacts with platelets, was used to confirm proper preparation of PPP to study platelet-independent effects of our peptide. Samples without calcium, where no clot was observed at any timepoint, served as negative controls. Untreated vehicle (1×DPBS) samples were used as a standard to compare peptide dosing impacts. For each sample, n=6 repeats were conducted. Coagulation profiles were obtained by measuring well absorbance at 405 nm (height 7.0 mm, 100 flashes) at 30 sec intervals for 60 min. Onset to clotting was detected as a sharp increase in sample turbidity.

In vivo studies. All animal experiments were conducted in accordance with the guidelines established by the Institutional Animal Care and Use Committee at the University of California, San Diego and the Association for the Assessment and Accreditation of Laboratory Animal Care and approved by the Institutional Animal Care and Use Committee at UCSD (A3033-01). Female Sprague Dawley rats (225-250 g) were used in all studies.

Intramyocardial injections of peptide into infarcted rats. MI was performed via 35-min ischemia-reperfusion and intramyocardial injections were performed under isoflurane, using a previously described procedure.[74,75] Briefly, cyclic peptide (75 μL, 0.75 μmol) was administered as a single injection into the infarct with a 27 G needle at 7 days post-MI. Animals were euthanized with an overdose of pentobarbital (200 mg/kg) at 24 hours post-injection (n=5).

Cryo-sectioning, histology, and immunofluorescence imaging. After euthanasia, hearts were resected, fresh frozen in TissueTek OCT, and cryosectioned for histological analysis. Slides were either stained with hematoxylin and eosin (H&E) to identify the infarct region or stained for immunofluorescence analysis. H&E slides were imaged on an Aperio ScanScope $CS^2$ at 20× magnification. For immunofluorescence, tissue sections were permeabilized in acetone (−20° C.) for 1.5 min and blocked with 2% BSA and 0.3% Triton X-100 in PBS. Myocardium was labeled using mouse anti-α-actinin antibody (1:800 dilution in blocking buffer, 1 hr incubation, Sigma-Aldrich) and an Alexa Fluor 488 goat anti-mouse IgG secondary antibody (1:500 dilution in blocking buffer, 30 min incubation, Life Technologies). Nuclei were labeled using Hoechst 33342 (0.1 μg/mL in DI water, 10 min incubation, Life Technologies). Slides were then imaged using a Leica Ariol slide scanner with Ariol software at 20× magnification.

Statistical analysis. All statistical results are expressed as mean±standard error (SEM). Ordinary one-way ANOVA tests were used for multiple comparisons of the mean in each group with that of the standard. Tukey corrections with 95% confidence intervals and significance were used. Two-way ANOVA tests without matching were used for multiple comparisons of the mean in each group at each timepoint with that of the standard. Holm-Sidak test was used for multiple comparisons. Statistical significance was defined as follows: ns ($p > 0.05$), *($p \leq 0.001$), **($p \leq 0.0001$).

These and other embodiments of the invention will be apparent to one skilled in the art upon a review of the present invention.

TABLE 1

FibPredictor experimental setup over three generations.

| | Generation 1 | Generation 2 | Generation 3 |
|---|---|---|---|
| Number of strands per sheet | 2 | 4 | 4 |
| Sense of β-sheet orientation | Both | Antiparallel or parallel | Selected in Gen 2 |
| Scoring function(s) | Amb_3b_score only | Amb_3b and GOAP score | Amb_3b and GOAP score |
| Rotations | x, z, zx, no rotation | x, z, zx, no rotation | x, z, zx, no rotation |
| Random models | 30 | 60 | 200 |
| Distance variation between the sheets | 7 Å | 7 Å | 6 Å |
| Minimum distance between the sheets | 3 Å | 3 Å | 4 Å |
| Angle variation between the sheets | 45° | 45° | 10° |

Input included the peptide sequence, number of strands per sheet (×2 sheets total) to model, and selection criterion about scoring functions, and rotation classes of amyloid fibrils. The number of random models, and distances angle variation between sheets, were also selected to improve modeling conditions. Changes to parameters with each future generation were a result of model analysis from the (n−1) generation.

TABLE 2

Experimental CD and theoretical modeling of gelators.

| Peptide | Sequence | Obs. CD π→π* Peak | Obs. CD Inference | Theor. CD Orientation | SCWRL4 energy | Amb_3b score | GOAP score | GOAP normalized |
|---|---|---|---|---|---|---|---|---|
| KLDL (SEQ ID NO: 5) | (KLDL)₃ (SEQ ID NO: 3) | — | antiparallel | antiparallel | 353.796 | −96.984 | −7271.93 | −75.7493 |
| KLDL (SEQ ID NO: 5)$_{Control}$ | LAG(KLDL)₃PLG (SEQ ID NO: 8) | Blue-shifted | Parallel | Parallel | 351.78 | −112.363 | −7675.04 | −53.2989 |
| KLDL (SEQ ID NO: 5)$_{Linear}$ | C(KLDL)₃PLGLAGC (SEQ ID NO: 6) | Blue-shifted | Parallel | Parallel | 370.407 | −128.576 | −8610.19 | −53.8137 |
| KFDF (SEQ ID NO: 1) | (KFDF)₃ (SEQ ID NO: 4) | — | Antiparallel | Antiparallel | 621.622 | −53.771 | −7179.08 | −74.7821 |
| KFDF (SEQ ID NO: 1)$_{Control}$ | LAG(KFDF)₃PLG (SEQ ID NO: 9) | Blue-shifted | Parallel | Parallel | 262.448 | −158.008 | −7755.24 | −53.8558 |
| KFDF (SEQ ID NO: 5)$_{Linear}$ | C(KFDF)₃PLGLAGC (SEQ ID NO: 7) | Blue-shifted | parallel | parallel | 340.488 | −158.782 | −11096.7 | −69.3543 |

Supplementary data to FIG. 2-3 in main text. Observed shift in high energy minimum in CD spectra indicate reorientation in 2° structure. Calculated orientations for minimal total energy structures generated in FibPredictor agree with observed inferences. Internal scoring SCWRL4 energies and corresponding empirical (Amber_3b) and statistical (SCWRL4) scores for minimal energy models are displayed for the top model of each sequence. Normalized GOAP scores are provided for comparison of fibrils of different sizes. Scores are unitless.

TABLE 3

DisConnect analysis of Rho-KLDL(SEQ ID NO: 5)$_{Cyclic}$ progelator.

| Peak | Sequence | SEQ ID NO(S) | m/z | Z(+) | Conclusion |
|---|---|---|---|---|---|
| A | BC1\|KLDLPLGLAGC2 | 15 | 806.36/1612.72 | 1 and 2 | All Cys connected |
| A | BC1K\|LDLPLGLAGC2 | 16 | 806.36/1612.72 | 1 and 2 | All Cys connected |
| A | BC1KL\|DLPLGLAGC2 | 57 | 806.36/1612.72 | 1 and 2 | All Cys connected |
| A | BC1KLD\|LPLGLAGC2 | 18&19 | 806.36/1612.72 | 1 and 2 | All Cys connected |
| A | BC1KLDL\|PLGLAGC2 | 20&21 | 806.36/1612.72 | 1 and 2 | All Cys connected |
| B | DLKLDLKLDLPLGLAG | 22 | 837.98 | 2 | 0\|0\|0\|0 |
| B | KLDLKLDLKLDLPLG | 23 | 837.995 | 2 | 0\|0\|0\|0 |
| C | BC1K\|DLKLDLPLGLAGC2 | 58 | 984.46 | 2 | All Cys connected |
| C | BC1KLD\|KLDLPLGLAGC2 | 18&15 | 984.46 | 2 | All Cys connected |
| C | BC1KLDLK\|DLPLGLAGC2 | 24&59 | 984.46 | 2 | All Cys connected |
| C | BC1KLDLKLD\|PLGLAGC2 | 25&21 | 984.46 | 2 | All Cys connected |
| D | BC1\|KLDLKLDLPLGLAGC2 | 60 | 1041 | 2 | All Cys connected |
| D | BC1K\|LDLKLDLPLGLAGC2 | 61 | 1041 | 2 | All Cys connected |
| D | BC1KL\|DLKLDLPLGLAGC2 | 62 | 1041 | 2 | All Cys connected |
| D | BC1KLD\|LKLDLPLGLAGC2 | 18&63 | 1041 | 2 | All Cys connected |
| D | BC1KLDL\|KLDLPLGLAGC2 | 20&64 | 1041 | 2 | All Cys connected |
| D | BC1KLDLK\|LDLPLGLAGC2 | 26&65 | 1041 | 2 | All Cys connected |
| D | BC1KLDLKL\|DLPLGLAGC2 | 27&66 | 1041 | 2 | All Cys connected |
| D | BC1KLDLKLD\|LPLGLAGC2 | 28&19 | 1041 | 2 | All Cys connected |
| D | BC1KLDLKLDL\|PLGLAGC2 | 29&21 | 1041 | 2 | All Cys connected |
| E | BC1K\|LKLDLKLDLPLGLAGC2 | 67 | 1161.59 | 2 | All Cys connected |

TABLE 3-continued

DisConnect analysis of Rho-KLDL(SEQ ID NO: 5)$_{Cyclic}$ progelator.

| Peak | Sequence | SEQ ID NO(S) | m/z | Z(+) | Conclusion |
|---|---|---|---|---|---|
| E | BC1KL\|KLDLKLDLPLGLAGC2 | 68 | 1161.59 | 2 | All Cys connected |
| E | BC1KLDLK\|LKLDLPLGLAGC2 | 30&69 | 1161.59 | 2 | All Cys connected |
| E | BC1KLDLKL\|KLDLPLGLAGC2 | 31&70 | 1161.59 | 2 | All Cys connected |
| E | BC1KLDLKLDLK\|LPLGLAGC2 | 32&71 | 1161.59 | 2 | All Cys connected |
| E | BC1KLDLKLDLKL\|PLGLAGC2 | 33&72 | 1161.59 | 2 | All Cys connected |
| F | BC1KLDLKLDLKLD\|LGLAGC2 | 34&73 | 1170.58 | 2 | All Cys connected |
| F | BC1KLDLKLDLKLDL\|GLAGC2 | 35&74 | 1170.58 | 2 | All Cys connected |
| G | BC1KL\|LKLDLKLDLPLGLAGC2 | 75 | 1218.13 | 2 | All Cys connected |
| G | BC1KLDLKL\|LKLDLPLGLAGC2 | 36&76 | 1218.13 | 2 | All Cys connected |
| G | BC1KLDLKLDLKL\|LPLGLAGC2 | 37&77 | 1218.13 | 2 | All Cys connected |
| H | BC1KL\|LGLAGC2 | 78 | 1287.56 | 1 | All Cys connected |
| H | BC1KLD\|GLAGC2 | 18&79 | 1289.51 | 1 | All Cys connected |
| H | BC1KLDLK\|GC2 | 38 | 1289.54 | 1 | All Cys connected |
| I | BC1KLD\|LGLAGC2 | 18&80 | 1402.59 | 1 | All Cys connected |
| I | BC1KLDL\|GLAGC2 | 20&81 | 1402.59 | 1 | All Cys connected |
| I | BC1KLDLKL\|GC2 | 39 | 1402.62 | 1 | All Cys connected |
| J | BC1KL\|LPLGLAGC2 | 82 | 1497.69 | 1 | All Cys connected |
| J | BC1K\|DLPLGLAGC2 | 83 | 1499.64 | 1 | All Cys connected |
| J | BC1KLD\|PLGLAGC2 | 18&84 | 1499.64 | 1 | All Cys connected |
| K | BC1KLD\|DLPLGLAGC2 | 18&85 | 1727.75 | 1 | All Cys connected |

Data from DisConnect software displayed in tables with peak labels corresponding to FIGS. 16a-16d, MS² fragmentation sequences, mass and charge values, separate peptides linked through a cysteine disulfide bond.

TABLE 4

DisConnect analysis of Rho-KFDF(SEQ ID NO: 1)$_{Cyclic}$ progelator.

| Peak | Sequence | SEQ ID NO(S) | m/z | Z(+) | Conclusion |
|---|---|---|---|---|---|
| A | BC1K\|DFKFDFPLGLAGC2 | 86 | 1035.445 | 2 | All Cys connected |
| A | BC1KFD\|KFDFPLGLAGC2 | 40&87 | 1035.445 | 2 | All Cys connected |
| A | BC1KFDFK\|DFPLGLAGC2 | 41&88 | 1035.445 | 2 | All Cys connected |
| A | BC1KFDFKFD\|PLGLAGC2 | 42&89 | 1035.445 | 2 | All Cys connected |
| B | KFDFKFDFKFDFPLGLAGC2 | 43 | 1104.035 | 2 | 69\|0\|0\|0 |
| C | BC1\|DFKFDFKFDFPLGLAGC2 | 90 | 1240.03 | 2 | All Cys connected |
| C | BC1KFD\|FDFKFDFPLGLAGC2 | 44&91 | 1240.03 | 2 | All Cys connected |
| C | BC1KFDF\|DFKFDFPLGLAGC2 | 45&92 | 1240.03 | 2 | All Cys connected |
| C | BC1KFDFKFD\|FDFPLGLAGC2 | 46&93 | 1240.03 | 2 | All Cys connected |
| C | BC1KFDFKFDF\|DFPLGLAGC2 | 47&94 | 1240.03 | 2 | All Cys connected |
| D | BC1KFDFKFDFKFDF\|GLAGC2 | 48&95 | 1272.545 | 2 | All Cys connected |
| E | BC1KFDFKFDFKFDFP\|LAGC2 | 49&96 | 1292.56 | 2 | All Cys connected |

TABLE 4-continued

DisConnect analysis of Rho-KFDF(SEQ ID NO: 1)$_{Cyclic}$ progelator.

| Peak | Sequence | SEQ ID NO(S) | m/z | Z(+) | Conclusion |
|---|---|---|---|---|---|
| E | BC1KFDFKFDFKFDFPL\|AGC2 | 50 | 1292.56 | 2 | All Cys connected |
| F | BC1K\|DFPLGLAGC2 | 97 | 1533.63 | 1 | All Cys connected |
| F | BC1KFD\|PLGLAGC2 | 51&98 | 1533.63 | 1 | All Cys connected |
| G | BC1\|KFDFPLGLAGC2 | 99 | 1680.7 | 1 | All Cys connected |
| G | BC1K\|FDFPLGLAGC2 | 100 | 1680.7 | 1 | All Cys connected |
| G | BC1KF\|DFPLGLAGC2 | 101 | 1680.7 | 1 | All Cys connected |
| G | BC1KFD\|FPLGLAGC2 | 52&102 | 1680.7 | 1 | All Cys connected |
| G | BC1KFDF\|PLGLAGC2 | 53&103 | 1680.7 | 1 | All Cys connected |
| H | BC1KFD\|DFPLGLAGC2 | 54&104 | 1795.73 | 1 | All Cys connected |
| I | BC1\|DFKFDFPLGLAGC2 | 105 | 1942.8 | 1 | All Cys connected |
| I | BC1KFD\|FDFPLGLAGC2 | 55&106 | 1942.8 | 1 | All Cys connected |
| I | BC1KFDF\|DFPLGLAGC2 | 56&107 | 1942.8 | 1 | All Cys connected |

Data from DisConnect software displayed in tables with peak labels and conclusions about cysteine connectivity. B is Rhodamine (413.15 m/z), | indicates separate peptides linked through a cysteine disulfide bond.

TABLE 5

Activated clotting times (ACT) in human blood.

| | standard | peptide in blood dilutions | | | | | | | positive control | negative control |
|---|---|---|---|---|---|---|---|---|---|---|
| | vehicle | 1:20000 | 1:10000 | 1:5000 | 1:1000 | 1:500 | 1:100 | 1:10 | collagen | no calcium |
| Average Time (sec) | 178 | 178 | 174 | 175 | 173 | 181 | 184 | 176 | 150 | >1500 |
| SEM | (±6) | (±3) | (±4) | (±6) | (±5) | (±5) | (±2) | (±3) | (±3) | n/a |
| P Value | | >0.9999 | 0.9941 | 0.9969 | 0.9787 | 0.9975 | 0.8982 | 0.9997 | 0.0002 | <0.0001 |
| Summary | | ns | ns | ns | ns | ns | ns | ns | *** | **** |

Supplemental data corresponding to FIG. 8a in the main text. Average times reported±standard error of mean (n=6 per group). Ordinary one-way ANOVA for comparison with vehicle standard. Values are mean±SEM.

TABLE 6

Hemolysis of red blood cells (RBCs).

| | standard | peptide in blood dilutions | | | | | | | positive control |
|---|---|---|---|---|---|---|---|---|---|
| | vehicle | 1:20000 | 1:10000 | 1:5000 | 1:1000 | 1:500 | 1:100 | 1:10 | 1% Triton X-100 |
| % Hemolysis | 0.00 | 0.20 | 0.37 | 0.30 | 0.13 | 0.26 | 0.40 | 4.43 | 100.00 |
| SEM | (±0.07) | (±0.06) | (±0.12) | (±0.08) | (±0.07) | (±0.26) | (±0.12) | (±0.64) | (±18.17) |
| P Value | | >0.9999 | >0.9999 | >0.9999 | >0.9999 | 0.9999 | >0.9999 | 0.9968 | <0.0001 |
| Summary | | ns | ns | ns | ns | ns | ns | ns | **** |

Supplemental data corresponding to FIG. 8c in the main text. Nonhemolytic biomaterials classified by <5% hemolysis. (n=4 per group). ns (p>0.05), *(p≤0.001), ** (p≤0.0001). Ordinary one-way ANOVA for comparison with vehicle standard. Values are mean±SEM.

REFERENCES

1. Mozaffarian, D. et al. Heart Disease and Stroke Statistics-2016 Update. Circulation 136, doi:10.1161/cir.0000000000000350 (2015).
2. Richardson, W. J., Clarke, S. A., Quinn, T. A. & Holmes, J. W. in Comprehensive Physiology (John Wiley & Sons, Inc., 2011).
3. Singelyn, J. M. et al. Naturally derived myocardial matrix as an injectable scaffold for cardiac tissue engineering. Biomaterials 30, 5409-5416, doi:https://doi.org/10.1016/j.biomaterials.2009.06.045 (2009).
4. Yu, J. et al. The effect of injected RGD modified alginate on angiogenesis and left ventricular function in a chronic rat infarct model. Biomaterials 30, 751-756, doi:https://doi.org/10.1016/j.biomaterials.2008.09.059 (2009).
5. Dorsey, S. M. et al. MRI evaluation of injectable hyaluronic acid-based hydrogel therapy to limit ventricular remodeling after myocardial infarction. Biomaterials 69, 65-75, doi:https://doi.org/10.1016/j.biomaterials.2015.08.011 (2015).
6. Lee, A. S. et al. Prolonged survival of transplanted stem cells after ischaemic injury via the slow release of pro-survival peptides from a collagen matrix. Nature Biomedical Engineering 2, 104-113, doi:10.1038/s41551-018-0191-4 (2018).
7. Losi, P. et al. Tissue response to poly(ether)urethane-polydimethylsiloxane-fibrin composite scaffolds for controlled delivery of pro-angiogenic growth factors. Biomaterials 31, 5336-5344, doi:https://doi.org/10.1016/j.biomaterials.2010.03.033 (2010).
8. Prokoph, S. et al. Sustained delivery of SDF-1α from heparin-based hydrogels to attract circulating pro-angiogenic cells. Biomaterials 33, 4792-4800, doi:https://doi.org/10.1016/j.biomaterials.2012.03.039 (2012).
9. Layman, H. et al. The effect of the controlled release of basic fibroblast growth factor from ionic gelatin-based hydrogels on angiogenesis in a murine critical limb ischemic model. Biomaterials 28, 2646-2654, doi:10.1016/j.biomaterials.2007.01.044 (2007).
10. Fujimoto, K. L. et al. Synthesis, characterization and therapeutic efficacy of a biodegradable, thermoresponsive hydrogel designed for application in chronic infarcted myocardium. Biomaterials 30, 4357-4368, doi:https://doi.org/10.1016/J.biomaterials.2009.04.055 (2009).
11. Bastings, M. M. C. et al. A Fast pH-Switchable and Self-Healing Supramolecular Hydrogel Carrier for Guided, Local Catheter Injection in the Infarcted Myocardium. Advanced Healthcare Materials 3, 70-78, doi:10.1002/adhm.201300076 (2014).
12. Wang, H. et al. Improved myocardial performance in infarcted rat heart by co-injection of basic fibroblast growth factor with temperature-responsive Chitosan hydrogel. The Journal of Heart and Lung Transplantation 29, 881-887, doi:https://doi.org/10.1016/j.healun.2010.03.016 (2010).
13. Formiga, F. R. et al. Controlled delivery of fibroblast growth factor-1 and neuregulin-1 from biodegradable microparticles promotes cardiac repair in a rat myocardial infarction model through activation of endogenous regeneration. Journal of Controlled Release 173, 132-139, doi:https://doi.org/10.1016/j.jconrel.2013.10.034 (2014).
14. Suarez, S. L. et al. Degradable Acetalated Dextran Microparticles for Tunable Release of an Engineered Hepatocyte Growth Factor Fragment. ACS Biomaterials Science & Engineering 2, 197-204, doi:10.1021/acsbiomaterials.5b00335 (2016).
15. Ungerleider, J. L. & Christman, K. L. Concise Review: Injectable Biomaterials for the Treatment of Myocardial Infarction and Peripheral Artery Disease: Translational Challenges and Progress. Stem Cells Translational Medicine 3, 1090-1099, doi:10.5966/sctm.2014-0049 (2014).
16. Hernandez, M. J. & Christman, K. L. Designing Acellular Injectable Biomaterial Therapeutics for Treating Myocardial Infarction and Peripheral Artery Disease. JACC: Basic to Translational Science 2, 212-226, doi:10.1016/j.jacbts.2016.11.008 (2017).
17. Portnov, T., Shulimzon Tiberiu, R. & Zilberman, M. in Reviews in Chemical Engineering Vol. 33 91 (2017).
18. Akiyama, N., Yamamoto-Fukuda, T., Takahashi, H. & Koji, T. In situ tissue engineering with synthetic self-assembling peptide nanofiber scaffolds, PuraMatrix, for mucosal regeneration in the rat middle-ear. International Journal of Nanomedicine 8, 2629-2640, doi:10.2147/IJN.S47279 (2013).
19. Davis, M. E. et al. Injectable Self-Assembling Peptide Nanofibers Create Intramyocardial Microenvironments for Endothelial Cells. Circulation 111, 442-450, doi:10.1161/01.CIR.0000153847.47301.80 (2005).
20. French, K. M., Somasuntharam, I. & Davis, M. E. Self-assembling peptide-based delivery of therapeutics for myocardial infarction. Advanced Drug Delivery Reviews 96, 40-53, doi:https://doi.org/10.1016/j.addr.2015.04.023 (2016).
21. Li, X. et al. Image-guided stem cells with functionalized self-assembling peptide nanofibers for treatment of acute myocardial infarction in a mouse model. American Journal of Translational Research 9, 3723-3731 (2017).
22. Yuan, X., He, B., Lv, Z. & Luo, S. Fabrication of self-assembling peptide nanofiber hydrogels for myocardial repair. RSC Advances 4, 53801-53811, doi:10.1039/C4RA08582E (2014).
23. Ravichandran, R., Venugopal, J. R., Sundarrajan, S., Mukherjee, S. & Ramakrishna, S. Minimally invasive cell-seeded biomaterial systems for injectable/epicardial implantation in ischemic heart disease. International Journal of Nanomedicine 7, 5969-5994, doi:10.2147/IJN.S37575 (2012).
24. Kalafatovic, D. et al. MMP-9 triggered micelle-to-fibre transitions for slow release of doxorubicin. Biomaterials Science 3, 246-249, doi:10.1039/C4BM00297K (2015).
25. Zhou, J. & Xu, B. Enzyme-Instructed Self-Assembly: A Multistep Process for Potential Cancer Therapy. Bioconjugate Chemistry 26, 987-999, doi:10.1021/acs.bioconjchem.5b00196 (2015).
26. Abul-Haija, Y. M. & Ulijn, R. V. in Hydrogels in Cell-Based Therapies 112-134 (The Royal Society of Chemistry, 2014).
27. Bowerman, C. J. & Nilsson, B. L. A Reductive Trigger for Peptide Self-Assembly and Hydrogelation. Journal of the American Chemical Society 132, 9526-9527, doi:10.1021/ja1025535 (2010).
28. Chien, M.-P. et al. Enzyme-Directed Assembly of Nanoparticles in Tumors Monitored by in Vivo Whole Animal Imaging and ex Vivo Super-Resolution Fluorescence Imaging. Journal of the American Chemical Society 135, 18710-18713, doi:10.1021/ja408182p (2013).
29. Nguyen, M. M. et al. Enzyme-Responsive Nanoparticles for Targeted Accumulation and Prolonged Retention in Heart Tissue after Myocardial Infarction. Advanced Materials 27, 5547-5552, doi:10.1002/adma.201502003 (2015).

30 Callmann, C. E. et al. Therapeutic Enzyme-Responsive Nanoparticles for Targeted Delivery and Accumulation in Tumors. Advanced Materials 27, 4611-4615, doi:10.1002/adma.201501803 (2015).

31 Spinale, F. G. Myocardial Matrix Remodeling and the Matrix Metalloproteinases: Influence on Cardiac Form and Function. Physiological Reviews 87, 1285-1342, doi: 10.1152/physrev.00012.2007 (2007).

32 Prabhu, S. D. & Frangogiannis, N. G. The Biological Basis for Cardiac Repair After Myocardial Infarction. From Inflammation to Fibrosis 119, 91-112, doi:10.1161/circresaha.116.303577 (2016).

33 Vulesevic, B., Sirois, M. G., Allen, B., de Denus, S. & White, M. Subclinical Inflammation in Heart Failure: A Neutrophil Perspective. Canadian Journal of Cardiology, doi:https://doi.org/10.1016/j.cjca.2018.01.018 (2018).

34 Rad-Malekshahi, M., Lempsink, L., Amidi, M., Hennink, W. E. & Mastrobattista, E. Biomedical Applications of Self-Assembling Peptides. Bioconjugate Chemistry 27, 3-18, doi:10.1021/acs.bioconjchem.5b00487 (2016).

35 Koutsopoulos, S. Self-assembling peptide nanofiber hydrogels in tissue engineering and regenerative medicine: Progress, design guidelines, and applications. Journal of Biomedical Materials Research Part A 104, 1002-1016, doi:doi:10.1002/jbm.a.35638 (2016).

36 Betush, R. J., Urban, J. M. & Nilsson, B. L. Balancing hydrophobicity and sequence pattern to influence self-assembly of amphipathic peptides. Peptide Science 110, e23099, doi:doi:10.1002/bip.23099 (2018).

37 Hamley, I. W. et al. Self-assembly of a model amphiphilic oligopeptide incorporating an arginine headgroup. Soft Matter 9, 4794-4801, doi:10.1039/C3SM50303H (2013).

38 Gao, J. et al. Controlling Self-Assembling Peptide Hydrogel Properties through Network Topology. Biomacromolecules 18, 826-834, doi:10.1021/acs.biomac.6b01693 (2017).

39 Tripathi, J. K. et al. Variants of self-assembling peptide, KLD-12 that show both rapid fracture healing and antimicrobial properties. Biomaterials 56, 92-103, doi:http://dx.doi.org/10.1016/j.biomaterials.2015.03.046 (2015).

40 Sun, J. et al. Biocompatibility of KLD-12 peptide hydrogel as a scaffold in tissue engineering of intervertebral discs in rabbits. Journal of Huazhong University of Science and Technology [Medical Sciences] 30, 173-177, doi:10.1007/s11596-010-0208-z (2010).

41 Kisiday, J. et al. Self-assembling peptide hydrogel fosters chondrocyte extracellular matrix production and cell division: Implications for cartilage tissue repair. Proceedings of the National Academy of Sciences 99, 9996-10001, doi:10.1073/pnas.142309999 (2002).

42 Tabatabaei Ghomi, H., Topp, E. M. & Lill, M. A. Fibpredictor: a computational method for rapid prediction of amyloid fibril structures. Journal of Molecular Modeling 22, 206, doi:10.1007/s00894-016-3066-1 (2016).

43 Zhang, S., Zhao, X. & Spirio, L. in Encyclopedia of Biomedical Polymers and Polymeric Biomaterials Vol. 11 (ed Munmaya K. Mishra) 15 (CRC Press, 2015).

44 Roeters, S. J. et al. Evidence for Intramolecular Antiparallel Beta-Sheet Structure in Alpha-Synuclein Fibrils from a Combination of Two-Dimensional Infrared Spectroscopy and Atomic Force Microscopy. Scientific Reports 7, 41051, doi:10.1038/srep41051 (2017).

45 Bulheller, B. M. & Hirst, J. D. DichroCalc-circular and linear dichroism online. Bioinformatics 25, 539-540, doi:10.1093/bioinformatics/btp016 (2009).

46 Khakshoor, O., Demeler, B. & Nowick, J. S. Macrocyclic R-Sheet Peptides That Mimic Protein Quaternary Structure through Intermolecular R-Sheet Interactions. Journal of the American Chemical Society 129, 5558-5569, doi: 10.1021/ja068511u (2007).

47 Hourani, R. et al. Processable Cyclic Peptide Nanotubes with Tunable Interiors. Journal of the American Chemical Society 133, 15296-15299, doi:10.1021/ja2063082 (2011).

48 Montenegro, J., Ghadiri, M. R. & Granja, J. R. Ion Channel Models Based on Self-Assembling Cyclic Peptide Nanotubes. Accounts of Chemical Research 46, 2955-2965, doi:10.1021/ar400061d (2013).

49 Dinerman, J. L. et al. Increased neutrophil elastase release in unstable angina pectoris and acute myocardial infarction. Journal of the American College of Cardiology 15, 1559-1563, doi:https://doi.org/10.1016/0735-1097(90)92826-N (1990).

50 van den Burg, B. & Eijsink, V. in Handbook of Proteolytic Enzymes (ed Guy Salvesen) 540-553 (Academic Press, 2013).

51 Grover, G. N., Braden, R. L. & Christman, K. L. Oxime Cross-Linked Injectable Hydrogels for Catheter Delivery. Advanced Materials 25, 2937-2942, doi:10.1002/adma.201205234 (2013).

52 Seif-Naraghi, S. B. et al. Safety and Efficacy of an Injectable Extracellular Matrix Hydrogel for Treating Myocardial Infarction. Science Translational Medicine 5, 173ra125-173ra125, doi:10.1126/scitranslmed.3005503 (2013).

53 Horton, S. & Augustin, S. in Monagle P. (eds) Haemostasis Vol. 992 Methods in Molecular Biology 155-167 (Humana Press, 2013).

54 Autian, J. in Kronenthal R. L., Oser Z., Martin E. (eds) Polymers in Medicine and Surgery Vol. 8 Polymer Science and Technology 181-203 (Springer).

55 Hee, K. S. et al. Self-Assembling Peptide Nanofibers Coupled with Neuropeptide Substance P for Bone Tissue Engineering. Tissue Engineering Part A 21, 1237-1246, doi:10.1089/ten.tea.2014.0472 (2015).

56 Zhu, J. & Marchant, R. E. Design properties of hydrogel tissue-engineering scaffolds. Expert review of medical devices 8, 607-626, doi:10.1586/erd.11.27 (2011).

57 Gawaz, M. Role of platelets in coronary thrombosis and reperfusion of ischemic myocardium. Cardiovascular Research 61, 498-511, doi:10.1016/j.cardiores.2003.11.036 (2004).

58 Roberts, D. E., McNicol, A. & Bose, R. Mechanism of Collagen Activation in Human Platelets. Journal of Biological Chemistry 279, 19421-19430, doi:10.1074/jbc.M308864200 (2004).

59 Seif-Naraghi, S. B. et al. Safety and efficacy of an injectable extracellular matrix hydrogel for treating myocardial infarction. Science translational medicine 5, 10.1126/scitranslmed.3005503, doi:10.1126/scitranslmed.3005503 (2013).

60 Kim, S. J. et al. Therapeutic effects of neuropeptide substance P coupled with self-assembled peptide nanofibers on the progression of osteoarthritis in a rat model. Biomaterials 74, 119-130, doi:https://doi.org/10.1016/j.biomaterials.2015.09.040 (2016).

61 Lu, J. et al. A neurotrophic peptide-functionalized self-assembling peptide nanofiber hydrogel enhances rat sciatic nerve regeneration. Nano Research, doi:10.1007/s12274-018-2041-9 (2018).

62 Wu, X. et al. Functional self-assembling peptide nanofiber hydrogel for peripheral nerve regeneration. Regenerative Biomaterials 4, 21-30, doi:10.1093/rb/rbw034 (2017).

63 Zhang, N., Luo, Y., He, L., Zhou, L. & Wu, W. A self-assembly peptide nanofibrous scaffold reduces inflammatory response and promotes functional recovery in a mouse model of intracerebral hemorrhage. Nanomedicine: Nanotechnology, Biology and Medicine 12, 1205-1217, doi:https://doi.org/10.1016/j.nano.2015.12.387 (2016).

64 Yu, H., Xiao, Y. & Guo, H. From Spirolactam Mixtures to Regioisomerically Pure 5- and 6-Rhodamines: A Chemodosimeter-Inspired Strategy. Organic Letters 14, 2014-2017, doi:10.1021/ol300523m (2012).

65 Reddy, K. M. B. et al. Large Scale Solid Phase Synthesis of Peptide Drugs: Use of Commercial Anion Exchange Resin as Quenching Agent for Removal of Iodine during Disulphide Bond Formation. International Journal of Peptides 2012, 8, doi:10.1155/2012/323907 (2012).

66 Mierke, D. F., Yamazaki, T., Said-Nejad, O. E., Felder, E. R. & Goodman, M. Cis/trans isomers in cyclic peptides without N-substituted amides. Journal of the American Chemical Society 111, 6847-6849, doi:10.1021/ja00199a058 (1989).

67 Nguyen, K., Iskandar, M. & Rabenstein, D. L. Kinetics and Equilibria of Cis/Trans Isomerization of Secondary Amide Peptide Bonds in Linear and Cyclic Peptides. The Journal of Physical Chemistry B 114, 3387-3392, doi:10.1021/jp1000286 (2010).

68 Bhattacharyya, M., Gupta, K., Gowd, K. H. & Balaram, P. Rapid mass spectrometric determination of disulfide connectivity in peptides and proteins. Molecular BioSystems 9, 1340-1350, doi:10.1039/C3MB25534D (2013).

69 Ghomi, H. T., Thompson, J. J. & Lill, M. A. Are distance-dependent statistical potentials considering three interacting bodies superior to two-body statistical potentials for protein structure prediction? Journal of Bioinformatics and Computational Biology 12, 1450022, doi: 10.1142/s021972001450022x % m 25212727 (2014).

70 Zhou, H. & Skolnick, J. GOAP: A Generalized Orientation-Dependent, All-Atom Statistical Potential for Protein Structure Prediction. Biophysical Journal 101, 2043-2052, doi:10.1016/j.bpj.2011.09.012 (2011).

71 Girardi, L., Sudi, K. & Muntean, W. Effect of Heparin, Platelets, Activated Platelets, Platelet Fragments, and Hematocrit on Activated Clotting Time. Artificial Organs 24, 507-513, doi:10.1046/j.1525-1594.2000.06552.x (2000).

72 Motlagh, D., Yang, J., Lui, K. Y., Webb, A. R. & Ameer, G. A. Hemocompatibility evaluation of poly(glycerol-sebacate) in vitro for vascular tissue engineering. Biomaterials 27, 4315-4324, doi:https://doi.org/10.1016/j.biomaterials.2006.04.010 (2006).

73 Evans, B. C. et al. Ex Vivo Red Blood Cell Hemolysis Assay for the Evaluation of pH-responsive Endosomolytic Agents for Cytosolic Delivery of Biomacromolecular Drugs. Journal of Visualized Experiments: JoVE, 50166, doi:10.3791/50166 (2013).

74 Seif-Naraghi, S. B., Horn, D., Schup-Magoffin, P. A. & Christman, K. L. Injectable extracellular matrix derived hydrogel provides a platform for enhanced retention and delivery of a heparin-binding growth factor. Acta biomaterialia 8, 3695-3703, doi:10.1016/j.actbio.2012.06.030 (2012).

75 Johnson, T. D., Braden, R. L. & Christman, K. L. Injectable ECM Scaffolds for Cardiac Repair. Methods in molecular biology (Clifton, N.J.) 1181, 109-120, doi: 10.1007/978-1-4939-1047-2_10 (2014).

---

The invention claimed is:

1. A tissue scaffolding composition comprising a pharmaceutically acceptable carrier and a cyclic peptide having a substrate recognition sequence that when enzymatically cleaved linearizes and self-assembles with like-kind peptides into a hydrogel, wherein the cyclic peptide is disulfide bonded by terminal cysteine residues and comprises repeating amino acid sequence KFDF (SEQ ID NO:1) and wherein the peptide self-assembles into a hydrogel via beta-sheets.

2. The composition of claim 1, wherein the substrate recognition sequence is specific for inflammatory-related enzymes, matrix metalloproteinases (MMP)-2/9 and/or elastase.

3. The composition of claim 1, wherein therapeutic peptide comprises a MMP-2/9 cleavable substrate recognition amino acid sequence PLGLAG (SEQ ID NO:2).

4. The composition of claim 1, wherein the peptide is labeled for detection.

5. The composition of claim 1, wherein the composition further comprises a therapeutic agent, a chemotactic agent, an antibiotic, or a growth factor.

6. The composition of claim 1, wherein the peptide comprises the amino acid sequence CKFDFKFDFKFDFPLGLAGC (SEQ ID NO:7).

7. A method of creating a scaffold for tissue repair in a patient in need thereof comprising administering to the patient a cyclic peptide having a substrate recognition sequence that when enzymatically cleaved linearizes and self-assembles with like-kind peptides into a hydrogel, wherein the cyclic peptide has a disulfide bonded by terminal cysteine residues and comprises repeating amino acid sequence KFDF (SEQ ID NO:1) and wherein the peptide self-assembles into a hydrogel via beta-sheets.

8. The method of claim 7, wherein the substrate recognition sequence is specific for inflammatory-related enzymes, matrix metalloproteinases (MMP)-2/9 and/or elastase.

9. The method of claim 7, wherein the peptide comprises a MMP-2/9 cleavable substrate recognition amino acid sequence PLGLAG (SEQ ID NO:2).

10. The method of claim 7, wherein the peptide is labeled for detection.

11. The method of claim 7, wherein the composition further comprises a therapeutic agent, a chemotactic agent, an antibiotic, or a growth factor.

12. The method of claim 7, wherein the tissue being repaired is ischemic tissue.

13. The method of claim 7, wherein the tissue being repaired is left ventricular tissue for remodeling post-myocardial infarction.

14. The method claim 7, wherein the administration is via a catheter, parenteral injection, or implantation.

15. The method of claim 7, wherein the composition is a liquid when administered and gels upon in situ enzymatic cleavage.

16. The method of claim 7, wherein the peptide comprises the amino acid sequence CKFDFKFDFKFDFPLGLAGC (SEQ ID NO:7).

17. A peptide comprising the amino acid sequence CKFDFKFDFKFDFPLGLAGC (SEQ ID NO:7).

18. The peptide of claim 17, wherein the peptide is cyclic.

* * * * *

SEQUENCE LISTING

<160> NUMBER OF SEQ ID NOS: 108

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Phe Asp Phe
1

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Leu Gly Leu Ala Gly
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Lys Leu Asp Leu Lys Leu Asp Leu Lys Leu Asp Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Phe Asp Phe Lys Phe Asp Phe Lys Phe Asp Phe
1               5                   10

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Leu Asp Leu
1

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Lys Leu Asp Leu Lys Leu Asp Leu Lys Leu Asp Leu Pro Leu Gly
1               5                   10                  15

Leu Ala Gly Cys
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Lys Phe Asp Phe Lys Phe Asp Phe Lys Phe Asp Phe Pro Leu Gly
1               5                   10                  15

Leu Ala Gly Cys
            20

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Ala Gly Lys Leu Asp Leu Lys Leu Asp Leu Lys Leu Asp Leu Pro
1               5                   10                  15

Leu Gly

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Ala Gly Lys Phe Asp Phe Lys Phe Asp Phe Lys Phe Asp Phe Pro
1               5                   10                  15

Leu Gly

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Leu Ala Gly Lys Leu Asp Leu Lys Leu Asp Leu Lys Leu Asp Leu
1               5                   10                  15

Pro Leu Gly Cys
            20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Leu Ala Gly Lys Phe Asp Phe Lys Phe Asp Phe Lys Phe Asp Phe
1               5                   10                  15

Pro Leu Gly Cys
            20

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Ala Gly Cys
1

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 13

Cys Lys Phe Asp Phe Lys Phe Asp Phe Lys Phe Asp Phe Pro Leu Gly
1               5                   10                  15

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Lys Phe Asp Phe Lys Phe Asp Phe Lys Phe Asp Phe Pro Leu Gly
1               5                   10                  15

Leu Ala

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Leu Asp Leu Pro Leu Gly Leu Ala Gly Cys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Asp Leu Pro Leu Gly Leu Ala Gly Cys
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Leu Asp Leu Gly Leu Ala Gly Cys
1               5

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Lys Leu Asp
1

<210> SEQ ID NO 19
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Pro Leu Gly Leu Ala Gly Cys
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Lys Leu Asp Leu
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Pro Leu Gly Leu Ala Gly Cys
1               5

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Leu Lys Leu Asp Leu Lys Leu Asp Leu Pro Leu Gly Leu Ala Gly
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Leu Asp Leu Lys Leu Asp Leu Lys Leu Asp Leu Pro Leu Gly
1               5                   10                  15

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Cys Lys Leu Asp Leu Lys
1               5
```

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Cys Lys Leu Asp Leu Lys Leu Asp
1               5
```

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Cys Lys Leu Asp Leu Lys
1               5
```

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Cys Lys Leu Asp Leu Lys Leu
1               5
```

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Cys Lys Leu Asp Leu Lys Leu Asp
1               5
```

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Cys Lys Leu Asp Leu Lys Leu Asp Leu
1               5
```

<210> SEQ ID NO 30
<211> LENGTH: 6
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 30

Cys Lys Leu Asp Leu Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Lys Leu Asp Leu Lys Leu
1               5

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Lys Leu Asp Leu Lys Leu Asp Leu Lys
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Lys Leu Asp Leu Lys Leu Asp Leu Lys Leu
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Lys Leu Asp Leu Lys Leu Asp Leu Lys Leu Asp
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Cys Lys Leu Asp Leu Lys Leu Asp Leu Lys Leu Asp Leu
1               5                   10
```

```
<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Lys Leu Asp Leu Lys Leu
1               5

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Lys Leu Asp Leu Lys Leu Asp Leu Lys Leu
1               5                   10

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Lys Leu Asp Leu Lys
1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Lys Leu Asp Leu Lys Leu
1               5

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Lys Phe Asp
1

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41
```

Cys Lys Phe Asp Phe Lys
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Lys Phe Asp Phe Lys Phe Asp
1               5

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Phe Asp Phe Lys Phe Asp Phe Lys Phe Asp Phe Pro Leu Gly Leu
1               5                   10                  15

Ala Gly Cys

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Lys Phe Asp
1

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Cys Lys Phe Asp Phe
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Cys Lys Phe Asp Phe Lys Phe Asp
1               5

<210> SEQ ID NO 47
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Lys Phe Asp Phe Lys Phe Asp Phe
1               5

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Lys Phe Asp Phe Lys Phe Asp Phe Lys Phe Asp Phe
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Lys Phe Asp Phe Lys Phe Asp Phe Lys Phe Asp Phe Pro
1               5                   10

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Lys Phe Asp Phe Lys Phe Asp Phe Lys Phe Asp Phe Pro Leu
1               5                   10                  15

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Cys Lys Phe Asp
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Cys Lys Phe Asp
```

```
<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Lys Phe Asp Phe
1               5

<210> SEQ ID NO 54
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Cys Lys Phe Asp
1

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Lys Phe Asp
1

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Lys Phe Asp Phe
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Leu Pro Leu Gly Leu Ala Gly Cys
1               5

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
                           -continued
      peptide

<400> SEQUENCE: 58

Asp Leu Lys Leu Asp Leu Pro Leu Gly Leu Ala Gly Cys
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Leu Pro Leu Gly Leu Ala Gly Cys
1               5

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Leu Asp Leu Lys Leu Asp Leu Pro Leu Gly Leu Ala Gly Cys
1               5                   10                  15

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Asp Leu Lys Leu Asp Leu Pro Leu Gly Leu Ala Gly Cys
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Leu Lys Leu Asp Leu Pro Leu Gly Leu Ala Gly Cys
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Lys Leu Asp Leu Pro Leu Gly Leu Ala Gly Cys
1               5                   10

<210> SEQ ID NO 64
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Leu Asp Leu Pro Leu Gly Leu Ala Gly Cys
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Asp Leu Pro Leu Gly Leu Ala Gly Cys
1               5                   10

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Leu Pro Leu Gly Leu Ala Gly Cys
1               5

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Leu Lys Leu Asp Leu Lys Leu Asp Leu Pro Leu Gly Leu Ala Gly Cys
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Leu Asp Leu Lys Leu Asp Leu Pro Leu Gly Leu Ala Gly Cys
1               5                   10                  15

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69
```

```
Leu Lys Leu Asp Leu Pro Leu Gly Leu Ala Gly Cys
1               5                   10
```

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

```
Lys Leu Asp Leu Pro Leu Gly Leu Ala Gly Cys
1               5                   10
```

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Leu Pro Leu Gly Leu Ala Gly Cys
1               5
```

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Pro Leu Gly Leu Ala Gly Cys
1               5
```

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

```
Leu Gly Leu Ala Gly Cys
1               5
```

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

```
Gly Leu Ala Gly Cys
1               5
```

<210> SEQ ID NO 75
<211> LENGTH: 16
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 75

Leu Lys Leu Asp Leu Lys Leu Asp Leu Pro Leu Gly Leu Ala Gly Cys
1               5                   10                  15

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Lys Leu Asp Leu Pro Leu Gly Leu Ala Gly Cys
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Pro Leu Gly Leu Ala Gly Cys
1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Gly Leu Ala Gly Cys
1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Leu Ala Gly Cys
1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Gly Leu Ala Gly Cys
1               5

```
<210> SEQ ID NO 81
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Leu Ala Gly Cys
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Pro Leu Gly Leu Ala Gly Cys
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Leu Pro Leu Gly Leu Ala Gly Cys
1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Pro Leu Gly Leu Ala Gly Cys
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Leu Pro Leu Gly Leu Ala Gly Cys
1               5

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86
```

```
Asp Phe Lys Phe Asp Phe Pro Leu Gly Leu Ala Gly Cys
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Lys Phe Asp Phe Pro Leu Gly Leu Ala Gly Cys
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Phe Pro Leu Gly Leu Ala Gly Cys
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Pro Leu Gly Leu Ala Gly Cys
1               5

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Phe Lys Phe Asp Phe Lys Phe Asp Phe Pro Leu Gly Leu Ala Gly
1               5                   10                  15

Cys

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Phe Asp Phe Lys Phe Asp Phe Pro Leu Gly Leu Ala Gly Cys
1               5                   10

<210> SEQ ID NO 92
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Phe Lys Phe Asp Phe Pro Leu Gly Leu Ala Gly Cys
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Phe Asp Phe Pro Leu Gly Leu Ala Gly Cys
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Phe Pro Leu Gly Leu Ala Gly Cys
1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Leu Ala Gly Cys
1               5

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Leu Ala Gly Cys
1

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Asp Phe Pro Leu Gly Leu Ala Gly Cys
```

```
1               5
```

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

```
Pro Leu Gly Leu Ala Gly Cys
1               5
```

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

```
Lys Phe Asp Phe Pro Leu Gly Leu Ala Gly Cys
1               5                   10
```

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

```
Phe Asp Phe Pro Leu Gly Leu Ala Gly Cys
1               5                   10
```

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

```
Asp Phe Pro Leu Gly Leu Ala Gly Cys
1               5
```

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

```
Phe Pro Leu Gly Leu Ala Gly Cys
1               5
```

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic

```
                               peptide

<400> SEQUENCE: 103

Pro Leu Gly Leu Ala Gly Cys
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asp Phe Pro Leu Gly Leu Ala Gly Cys
1               5

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asp Phe Lys Phe Asp Phe Pro Leu Gly Leu Ala Gly Cys
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Phe Asp Phe Pro Leu Gly Leu Ala Gly Cys
1               5                   10

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Asp Phe Pro Leu Gly Leu Ala Gly Cys
1               5

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Gln Arg Phe Glu Trp Glu Phe Glu Gln Gln
1               5                   10
```